US008512944B2

(12) United States Patent
Nakamura et al.

(10) Patent No.: US 8,512,944 B2
(45) Date of Patent: Aug. 20, 2013

(54) PRMT1 FOR TARGET GENES OF CANCER THERAPY AND DIAGNOSIS

(75) Inventors: Yusuke Nakamura, Tokyo (JP); Ryuji Hamamoto, Tokyo (JP); Akira Togashi, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 13/060,672

(22) PCT Filed: Aug. 25, 2009

(86) PCT No.: PCT/JP2009/004091
§ 371 (c)(1),
(2), (4) Date: Jun. 21, 2011

(87) PCT Pub. No.: WO2010/023877
PCT Pub. Date: Mar. 4, 2010

(65) Prior Publication Data
US 2011/0160293 A1  Jun. 30, 2011

Related U.S. Application Data

(60) Provisional application No. 61/190,416, filed on Aug. 27, 2008.

(51) Int. Cl.
*C12Q 1/00* (2006.01)
(52) U.S. Cl.
USPC .......................................................... 435/4
(58) Field of Classification Search
None
See application file for complete search history.

(56) References Cited

U.S. PATENT DOCUMENTS

| 7,897,329 B2 | 3/2011 | Nakamura et al. |
| 7,939,254 B2 | 5/2011 | Nakamura et al. |
| 2006/0239990 A1 | 10/2006 | Nabel et al. |

FOREIGN PATENT DOCUMENTS

| CN | 1331326 A | 1/2002 |
| CN | 1339592 A | 3/2002 |
| EP | 2221053 A1 | 8/2010 |
| JP | 2008/514186 A | 5/2008 |
| JP | 2008/164517 A | 7/2008 |
| JP | 2008/530974 A | 8/2008 |
| JP | 2009/502113 A | 1/2009 |
| WO | WO 02/16568 A2 | 2/2002 |
| WO | WO 2005/060722 A2 | 7/2005 |
| WO | WO 2007/013574 A1 | 2/2007 |
| WO | WO 2007/067814 A2 | 6/2007 |
| WO | WO 2008/104077 A1 | 9/2008 |

OTHER PUBLICATIONS

Scorilas et al. (Biochemical and Biophysical Research Communications 2000 vol. 278 p. 349).*

Tang et al (JBC, 2000, 275(11): 7723-7730).*
Spannhoff et al (J Med Chem, 2007, 50: 2319-2325).*
Bauer, et al., "Methylation at arginine 17 of histone H3 is linked to gene activation," *EMBO Rep.*, vol. 3(1), pp. 39-44 (Jan. 2002, Epub Dec. 19, 2001).
Bedford, et al., "Arginine Methylation: An Emerging Regulator of Protein Function," *Mol Cell.*, vol. 18(3), pp. 263-272 (Apr. 29, 2005).
Boisvert, et al., "Protein Interfaces in Signaling Regulated by Arginine Methylation," *Sci STKE.*, vol. 2005(271), re2, 10 pages (Feb. 15, 2005).
Chen, et al., "Silencing SMYD3 in hepatoma demethylates RIZ1 promoter induces apoptosis and inhibits cell proliferation and migration," *World J Gastroenterol.*, vol. 13(43), pp. 5718-5724 (Nov. 21, 2007).
Cheung, et al., "Protein arginine-methyltransferase-dependent oncogenesis," *Nat Cell Biol.*, vol. 9(10), pp. 1208-1215 (Oct. 2007, Epub Sep. 23, 2007).
Cloos, et al., "The putative oncogene GASC1 demethylates tri- and dimethylated lysine 9 on histone H3," *Nature*, vol. 442(7100), pp. 307-311 (Jul. 20, 2006, Epub May 28, 2006).
Cook, et al., "FBXO11/PRMT9, a new protein arginine methyltransferase, symmetrically dimethylates arginine residues," *Biochem Biophys Res Commun.*, vol. 342(2), pp. 472-481 (Apr. 7, 2006, Epub Feb. 8, 2006).
Hamamoto, et al., "SMYD3 encodes a histone methyltransferase involved in the proliferation of cancer cells," *Nat. Cell Biol.*, vol. 6(8), pp. 731-740 (Aug. 2004, Epub Jul. 4, 2004)
Hamamoto, et al., "Enhanced SMYD3 expression is essential for the growth of breast cancer cells," *Cancer Sci.*, vol. 97(2), pp. 113-118 (Feb. 2006).
Hamamoto, et al., "Functional analysis of PRMT1, a histone arginine methyltransferase, in human carcinogenesis," *The 67th Annual Meeting of the Japanese Cancer Association*, vol. 310(#EW8-3), 1 page (Sep. 30, 2008).
Klose, et al., "The transcriptional repressor JHDM3A demethylates trimethyl histone H3 lysine 9 and lysine 36," *Nature*, vol. 442(7100), pp. 312-316 (Jul. 20, 2006, Epub May 28, 2006).
Kouzarides, "Histone methylation in transcriptional control," *Curr Opin Genet Dev.*, vol. 12(2), pp. 198-209 (Apr. 2002).

(Continued)

*Primary Examiner* — Sean Aeder
(74) *Attorney, Agent, or Firm* — Kilpatrick Townsend & Stockton LLP

(57) ABSTRACT

Objective methods for diagnosing a predisposition to developing cancer, particularly bladder cancer, gastric cancer, colorectal cancer, breast cancer, esophageal cancer, lung cancer, lymphoma, pancreatic cancer and testicular cancer, are described herein. In one embodiment, the diagnostic method involves determining an expression level of PRMT1 gene. The present invention further provides methods of screening for therapeutic agents useful in the treatment of PRMT1 associated disease, such as a cancer, e.g. bladder cancer, gastric cancer, colorectal cancer, breast cancer, esophageal cancer, lung cancer, lymphoma, pancreatic cancer and testicular cancer. The present invention further provides methods of inhibiting the cell growth and treating or alleviating symptoms of PRMT1 associated diseases. The present invention also features products, including double-stranded molecules and vectors encoding thereof as well as to compositions comprising them.

2 Claims, 3 Drawing Sheets

(56) References Cited

OTHER PUBLICATIONS

Kunizaki, et al., "The Lysine 831 of Vascular Endothelial Growth Factor Receptor 1 is a Novel Target of Methylation by SMYD3," *Cancer Res.*, vol. 67(22), pp. 10759-10765 (Nov. 15, 2007).

Liu, et al., "The Telomerase Reverse Transcriptase (hTERT) Gene is a Direct Target of the Histone Methyltransferase SMYD3," *Cancer Res.*, vol. 67(6), pp. 2626-2631 (Mar. 15, 2007).

Luger, et al., "Crystal structure of the nucleosome core particle at 2.8 A resolution," *Nature*, vol. 389(6648), pp. 251-260 (Sep. 18, 1997).

Margueron, et al., The key to development: interpreting the histone code?*Curr Opin Genet Dev.*, vol. 15(2), pp. 163-176 (Apr. 2005).

Martin, et al., "The Diverse Functions of Histone Lysine Methylation," *Nat Rev Mol Cell Biol.*, vol. 6(11), pp. 838-849 (Nov. 2005).

Pal, et al., "Human SWI/SNF-Associated PRMT5 Methylates Histone H3 Arginine 8 and Negatively Regulates Expression of ST7 and NM23 Tumor Suppressor Genes," *Mol Cell Biol.*, vol. 24(21), pp. 9630-9645 (Nov. 2004).

Schneider, et al., "Unsafe SETs: histone lysine methyltransferases and cancer," *Trends Biochem Sci.*, vol. 27(8), pp. 396-402 (Aug. 2002).

Schurter, et al., "Methylation of Histone H3 by Coactivator-Associated Arginine Methyltransferase 1," *Biochemistry*, vol. 40(19), pp. 5747-5756 (May 15, 2001).

Shi, et al., "Histone Demethylation Mediated by the Nuclear Amine Oxidase Homolog LSD1," *Cell*, vol. 119(7), pp. 941-953 (Dec. 29, 2004).

Silva et al, "Enhanced methyltransferase activity of SMYD3 by the cleavage of its N-terminal region in human cancer cells," *Oncogene*, vol. 27(19), pp. 2686-2692 (Apr. 24, 2008, Epub Nov. 12, 2007).

Sims, et al., "Histone lysine methylation: a signature for chromatin function," *Trends Genet.*, vol. 19(11), pp. 629-639 (Nov. 2003).

Sparmann, et al., "Polycomb silencers control cell fate, development and cancer," *Nat Rev Cancer*, vol. 6(11), pp. 846-856 (Nov. 2006).

Strahl, et al., "Methylation of histone H3 at lysine 4 is highly conserved and correlates with transcriptionally active nuclei in Tetrahymena," *Proc Natl Acad Sci USA*, vol. 96(26), pp. 14967-14972 (Dec. 21, 1999).

Takeshita, et al., "Efficient delivery of small interfering RNA to bone-metastatic tumors by using atelocollagen in vivo," *Proc Natl Acad Sci USA*, vol. 102(34), pp. 12177-12182 (Aug. 23, 2005, Epub Aug. 9, 2005).

Tsuge, et al., "A variable number of tandem repeats polymorphism in an E2F-1 binding element in the 5'flanking region of SMYD3 is a risk factor for human cancers," *Nat Genet.*, vol. 37(10), pp. 1104-1107 (Oct. 2005, Epub Sep. 11, 2005).

Tsukada, et al., "Histone demethylation by a family of JmjC domain-containing proteins," *Nature*, vol. 439(7078), pp. 811-816 (Feb. 16, 2006, Epub Dec. 18, 2005).

Wang, et al., "Methylation of Histone H4 at Arginine 3 Facilitating Transcriptional Activation by Nuclear Hormone Receptor," *Science*, vol. 293(5531), pp. 853-857 (Aug. 3, 2001, Epub May 31, 2001).

Yoshimatsu, et al., "Dysregulation of PRMT1 and PRMT6, Type I arginine methyltranserases, is involved in various types of human cancers," *Int J Cancer*, vol. 128(3), pp. 562-573 (Feb. 1, 2011).

Heinke, R., et al., "Virtual Screening and Biological Characterization of Novel Histone Arginine Methyltransferase PRMT1 Inhibitors," *ChemMedChem*, vol. 4, pp. 69-77 (Dec. 10, 2008, Wiley-VCH Verlag, Weinheim, DE).

Scorilas, A., et al., "Genomic Organization, Physical Mapping, and Expression Analysis of the Human Protein Arginine Methyltransferase 1 Gene," *Biochemical and Biophysical Research Communications*, vol. 278(2), pp. 349-359 (Nov. 19, 2000).

Spannhoff, A., et al., "A novel arginine methyltransferase inhibitor with cellular activity," *Bioorganic & Medicinal Chemistry Letters*, vol. 17(15), pp. 4150-4153 (Aug. 1, 2007, Jun. 3, 2007).

\* cited by examiner

PRMT1 FOR TARGET GENES OF CANCER THERAPY AND DIAGNOSIS

PRIORITY

The present application is a U.S. National Stage Application of PCT/JP2009/004091, filed Aug. 25, 2009, which claims the benefit of U.S. Provisional Application No. 61/190,416, filed on Aug. 27, 2008, the entire contents of which are incorporated by reference herein in their entirety.

TECHNICAL FIELD

1. Technical Field

The present invention relates to methods of detecting and diagnosing a predisposition to developing cancer, particularly bladder cancer, gastric cancer, colorectal cancer, breast cancer, esophageal cancer, lung cancer, lymphoma, pancreatic cancer and testicular cancer. The present invention also relates to methods of screening for a candidate compound for treating and preventing cancer with over-expression of PRMT1, particularly bladder cancer, gastric cancer, colorectal cancer, breast cancer, esophageal cancer, lung cancer, lymphoma, pancreatic cancer and testicular cancer. Moreover, the present invention relates to a double-stranded molecule which reduces PRMT1 gene expression and uses thereof. In particular, the present invention relates to PRMT1.

2. Background Art

The eukaryotic genome is packaged into chromatin that is an array of nucleosomes in each of which 146 base pairs (bp) of DNA are wrapped around an octamer of core histone proteins like H2A, H2B, H3 and H4 (NPL 1). Chromatin is a dynamic structure that modulates the access of regulatory factors to the genetic material. Thus, transcription and other cellular processes that require access to DNA are regulated by chromatin structure, and therefore, a precise coordination and organization of events in opening and closing the chromatin is crucial for these cellular processes to function normally. Histone methylation has emerged as an important platform for gene regulation. Specific lysines in histone H3 or H4 can be mono-, di-, or trimethylated, adding another layer of complexity to this mode of regulation (NPL 2). Moreover, these modifications may either signal activation (H3K4, H3K36, and H3K79), or the silencing (H3K9, H3K27, and H4K20) of gene expression (NPL 3-4). These effects on transcriptional regulation have biological consequences ranging from cell differentiation to X inactivation (NPL 3, 5-6). Historically, histone methylation was considered a permanent modification. However, in the past few years several groups have provided evidence for the existence of histone demethylases (NPL 7-10). Therefore, it is supposed that this modification may regulate physiological functions of cells dynamically and variedly.

The biological importance of the histone methylation system in diseases like cancer has become clearer through functional analysis of enzymes involved in these modifications. Histone methyltransferases (HMTases) are the enzymes responsible for these modifications and are specific for either lysine or arginine residues. While arginine methylation is catalyzed by the PRMT/CARM family of HMTase, lysine methylations are carried out by a SET-domain containing HMTase. Arginine methylation of histones and other nuclear proteins is performed by the family of PRMTs (protein arginine methyltransferases) that contains nine members in humans (NPL 11-12). PRMTs use S-adenosylmethionine (SAM)-dependent methylation to modify the guanidino nitrogens of the arginine side chain by adding one or two methyl groups (NPL 13). With regard to the dimethylation product, PRMTs are distinguished into type I enzymes, which catalyze the asymmetric NG, NG-di-methyl-arginine, and the type II which consists of PRMT5, PRMT7, and PRMT9 and generates symmetric NG, NG dimethylation (NPL 12-13). Similar to other histone modifications, histone arginine methylation contributes to transcriptional regulation and is catalyzed by a subset of family members: PRMT1 methylates H4/H2A at R3 (NPL 14), PRMT4/CARM1 (coactivator-associated arginine methyltransferase 1) methylates H3 at R17/R26 (NPL 15-16), and PRMT5 methylates H3 at R8 and H4/H2A at R3 (NPL 17). Histone-modifying PRMTs are recruited to the chromatin by their interaction with transcription factors and regulate gene activation as well as repression (NPL 12).

It was previously shown that SMYD3, a histone methyltransferase, stimulates proliferation of cells and plays an important role in human carcinogenesis through its methyltransferase activity (NPL 18-24). In addition, it was also indicated that some histone methyltransferases can also be relating to malignant alterations of human cells (NPL 25-27). According to this kind of evidence, dysfunction of histone methyltransferase can positively make a contribution to human carcinogenesis, but a general understanding of the relationship between abnormalities of histone methylation and cancer has not yet been clarified. The present invention addresses these and other needs.

Citation List

Non Patent Literature

[NPL 1] Luger K, et al., Nature 1997; 389:251-260
[NPL 2] Strahl B D, et al., Proc Natl Acad Sci USA 1999; 96:14967-14972
[NPL 3] Martin C and Zhang Y, Nat Rev Mol Cell Biol 2005; 6:838-849
[NPL 4] Sims R J, 3rd, et al., Trends Genet. 2003; 19:629-639
[NPL 5] Kouzarides T, Curr Opin Genet Dev 2002; 12:198-209
[NPL 6] Margueron R, et al., Curr Opin Genet Dev 2005; 15:163-176
[NPL 7] Tsukada Y, et al., Nature 2006; 439:811-816
[NPL 8] Shi Y, Lan F, et al., Cell 2004; 119:941-953
[NPL 9] Klose R J, et al., Nature 2006; 442:312-316
[NPL 10] Cloos P A, et al., Nature 2006; 442:307-311
[NPL 11] Boisvert F M, et al., Sci STKE 2005; 2005:re2
[NPL 12] Cook J R, et al., Biochem Biophys Res Commun 2006; 342:472-481
[NPL 13] Bedford M T and Richard S, Mol Cell 2005; 18:263-272
[NPL 14] Wang H, et al., Science 2001; 293:853-857
[NPL 15] Schurter B T, et al., Biochemistry 2001; 40:5747-5756
[NPL 16] Bauer U M, et al., EMBO Rep 2002; 3:39-44
[NPL 17] Pal S, et al., Mol Cell Biol 2004; 24:9630-9645
[NPL 18] Tsuge M, et al., Nat Genet. 2005; 37:1104-1107
[NPL 19] Liu C, et al., Cancer Res 2007; 67:2626-2631
[NPL 20] Hamamoto R, et al., Cancer Sci 2006; 97:113-118
[NPL 21] Hamamoto R, et al., Nat Cell Biol 2004; 6:731-740
[NPL 22] Chen L B, et al., World J Gastroenterol 2007; 13:5718-5724
[NPL 23] Kunizaki M, et al., Cancer Res 2007; 67:10759-10765
[NPL 24] Silva F P, et al., Oncogene 2008; 27:2686-2692
[NPL 25] Sparmann A and van Lohuizen M, Nat Rev Cancer 2006; 6:846-856

[NPL 26] Takeshita F, et al., Proc Natl Acad Sci USA 2005; 102:12177-12182

[NPL 27] Schneider R, et al., Trends Biochem Sci 2002; 27:396-402

SUMMARY OF INVENTION

In the present invention, the expression profiles of PRMT family members was confirmed in clinical tissues for the purpose of identifying a methyltransferase that can contribute to human carcinogenesis.

In the present invention, it was identified that PRMT1 was overexpressed in several cancer cells, through the RT-PCR. Since it was scarcely expressed in adult normal organs, PRMT1 is an appropriate and promising molecular target for a novel therapeutic approach with minimal adverse effect. Functionally, knockdown of endogenous PRMT1 by siRNA in cancer cell lines resulted in drastic suppression of cancer cell growth, demonstrating its essential role in maintaining viability of cancer cells.

Accordingly, the present invention features a method of diagnosing or determining a predisposition to cancer, particularly bladder cancer, gastric cancer, colorectal cancer, breast cancer, esophageal cancer, lung cancer, lymphoma, pancreatic cancer and testicular cancer in a subject by determining an expression level of PRMT1 in a subject derived biological sample, such as biopsy. An increase of the level of expression of PRMT1 compared to a normal control level indicates that the subject suffers from or is at risk of developing cancer, particularly bladder cancer, gastric cancer, colorectal cancer, breast cancer, esophageal cancer, lung cancer, lymphoma, pancreatic cancer and testicular cancer. In the methods, PRMT1 gene can be detected by appropriate probes or the PRMT1 protein can be detected by an anti-PRMT1 antibody.

The present invention further provides methods of identifying an agent that inhibits the expression of a PRMT1 gene or the activity of its gene product. Furthermore the present invention provides methods of identifying a candidate agent for treating or preventing PRMT1 associated-disease, such as cancer, e.g. bladder cancer, gastric cancer, colorectal cancer, breast cancer, esophageal cancer, lung cancer, lymphoma, pancreatic cancer and testicular cancer or a candidate agent that inhibits growth of cells over-expressing the PRMT1 gene. The method can be carried out in vitro or in vivo. A decrease in the expression level of the PRMT1 gene and/or biological activity of its gene product as compared to that in the absence of the test agent indicates that the test agent is an inhibitor of the PRMT1 and may be used to inhibit the growth of cells over-expressing the PRMT1 gene, such as cancerous cell, e.g. in bladder cancer, gastric cancer, colorectal cancer, breast cancer, esophageal cancer, lung cancer, lymphoma, pancreatic cancer and testicular cancer.

In another aspect, the present invention provides a method for inhibiting the growth of a cancerous cell over-expressing PRMT1 by administering an agent that inhibits expression of PRMT1 and/or function of the PRMT1 protein. Preferably the agent is an inhibitory nucleic acid (e.g., an anti-sense, ribozyme, double stranded molecule). The agent may be a nucleic acid molecule or vector for providing double stranded molecule. Expression of the gene may be inhibited by introduction of a double stranded molecule into the target cell in an amount sufficient to inhibit expression of the PRMT1 gene. The present invention also provides methods for inhibiting the growth of cancerous cells over-expressing PRMT1 in a subject. The methods are useful for treating or preventing cancer, particularly bladder cancer, gastric cancer, colorectal cancer, breast cancer, esophageal cancer, lung cancer, lymphoma, pancreatic cancer and testicular cancer. In another aspect, the present invention relates to a pharmaceutical composition for treating or preventing cancer that includes double-stranded molecules or vectors encoding them as an active ingredient and pharmaceutically acceptable carrier. The double-stranded molecules provided in the present invention have the property to inhibit expression of the PRMT1 gene and inhibit the growth of cancerous cells over-expressing PRMT1 when introduced into the cells. For example, such molecules target the sequence corresponding to the positions 803-821 of SEQ ID NO: 1. The molecules of the present invention comprise a sense strand and an antisense strand, wherein the sense strand comprises a sequence comprising the target sequence, and wherein the anti-sense strand comprises a sequence which is complementary to the sense strand. The sense and the anti-sense strands of the molecule hybridize to each other to form a double-stranded molecule.

DESCRIPTION OF EMBODIMENTS

Figure 1:
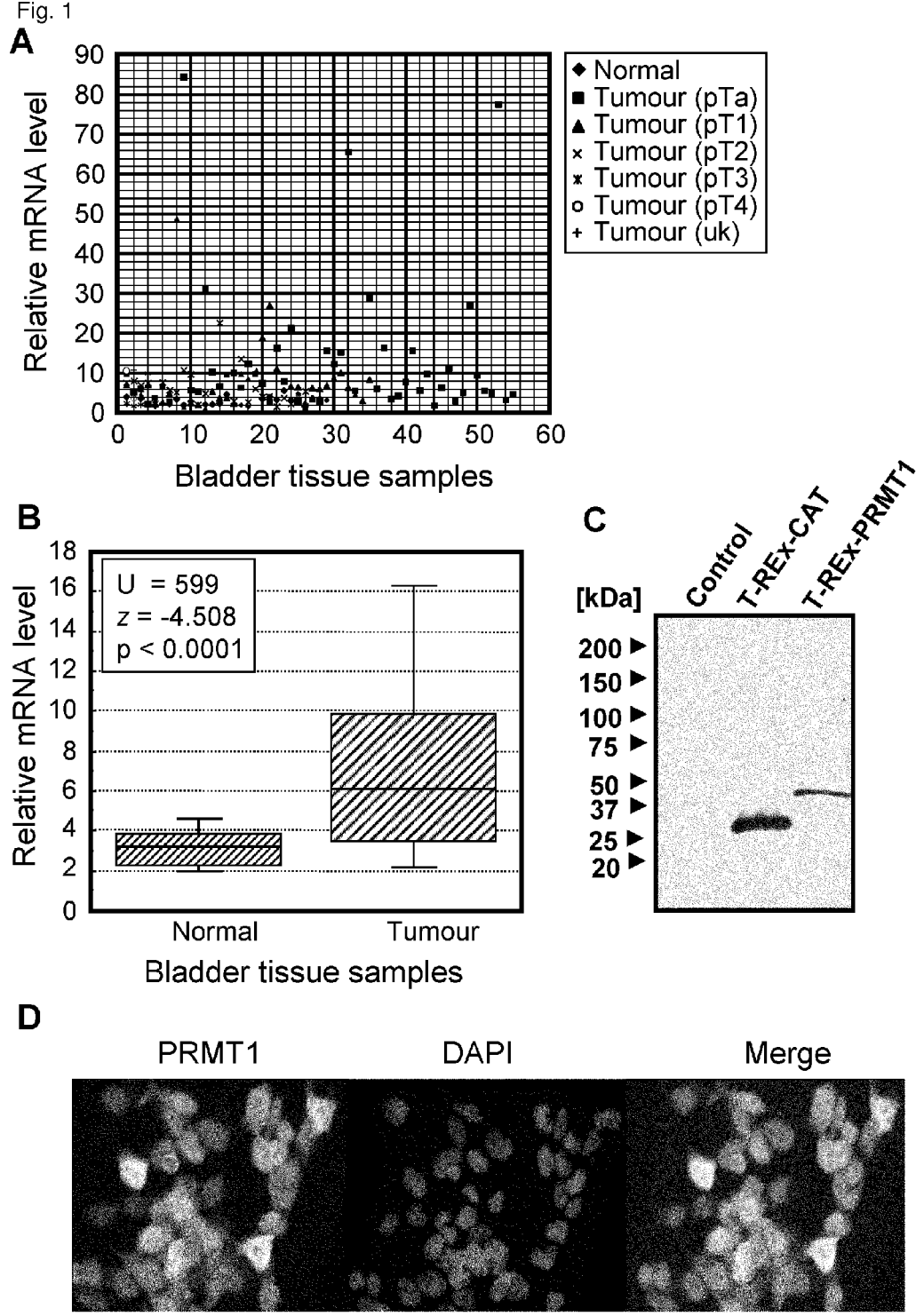
FIG. 1 depicts quantitative analysis of PRMT1 gene expressions in bladder tissues using quantitative RT-PCR and sub-cellular localization of PRMT1 protein. A, Expression profile of PRMT1. Quantitative RT-PCR was used to study gene expression in a cohort of bladder cancers and normal bladder samples. Relative gene expression was assessed using the method of Pfaffl, a modified method of comparative quantification. B, PRMT1 gene expression in normal and tumor tissues is shown by the box-whisker plot. P value was calculated using the Mann-Whitney U test. C, Western blot analysis of exogenously expressed V5-tagged PRMT1 protein in T-REx 293-PRMT1 cells. T-REx-293 (Mock) and T-REx-CAT were used as a negative control. D, V5-tagged PRMT1 protein was expressed exogenously into Flp-In T-REx cells, and stained with anti-V5 monoclonal antibody. The protein was visualized by Alexa546-conjugated secondary anti-mouse IgG antibody (left panel). Nuclei were counterstained with DAPI (middle panel). Merged image of Alexa546 and DAPI (right panel).

Definition:

The words "a", "an", and "the" as used herein mean "at least one" unless otherwise specifically indicated.

An "isolated" or "purified" nucleic acid molecule, such as a cDNA molecule, can be substantially free of other cellular material, or culture medium when produced by recombinant techniques, or substantially free of chemical precursors or other chemicals when chemically synthesized. In a preferred embodiment, nucleic acid molecules encoding antibodies of the present invention are isolated or purified.

The terms "polypeptide", "peptide", and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" refers to naturally occurring and synthetic amino acids, as well as amino acid analogs and amino acid mimetics that similarly functions to the naturally occurring amino acids. Naturally occurring amino acids are those encoded by the genetic code, as well as those modified after translation in cells (e.g., hydroxy-proline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "polynucleotides", "oligonucleotide", "nucleotides", "nucleic acids", and "nucleic acid molecules" are used interchangeably unless otherwise specifically indicated and, similarly to the amino acids, are referred to by their commonly accepted single-letter codes. Similar to the amino acids, they encompass both naturally-occurring and non-naturally occurring nucleic acid polymers. The polynucleotide, oligonucleotide, nucleotides, nucleic acids, or nucleic acid molecules may be composed of DNA, RNA or a combination thereof.

PRMT1 Gene or PRMT1 Protein:

The present invention is based in part on the discovery that the gene encoding PRMT1 is over-expressed in several cancers compared to non-cancerous tissue. The cDNA of PRMT1 is 1131 nucleotides in length. The nucleic acid and polypeptide sequences of PRMT1 are not to be considered limited to what is shown in SEQ ID NO: 1 and 2, respectively. The sequence data are also available via following accession numbers.

PRMT1: BC109283, NM_001536, NM_198319 or NM_198318 (the entire disclosures of which are herein incorporated by reference)

According to an aspect of the present invention, functional equivalents are also considered to be "PRMT1 polypeptides". Herein, a "functional equivalent" of a protein (e.g., a PRMT1 polypeptide) is a polypeptide that has a biological activity equivalent to the protein. Namely, any polypeptide that retains the biological ability of the PRMT1 protein may be used as such a functional equivalent in the present invention. Such functional equivalents include those wherein one or more amino acids are substituted, deleted, added, or inserted to the natural occurring amino acid sequence of the PRMT1 protein. Alternatively, the polypeptide may be composed an amino acid sequence having at least about 80% homology (also referred to as sequence identity) to the sequence of the respective protein, more preferably at least about 90% to 95% homology, often about 96%, 97%, 98% or 99% homology. In other embodiments, the polypeptide can be encoded by a polynucleotide that hybridizes under stringent conditions to the natural occurring nucleotide sequence of the PRMT1 gene.

A polypeptide of the present invention may have variations in amino acid sequence, molecular weight, isoelectric point, the presence or absence of sugar chains, or form, depending on the cell or host used to produce it or the purification method utilized. Nevertheless, so long as it has a function equivalent to that of the human PRMT1 protein of the present invention, it is within the scope of the present invention.

The phrase "stringent (hybridization) conditions" refers to conditions under which a nucleic acid molecule will hybridize to its target sequence, typically in a complex mixture of nucleic acids, but not detectably to other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10 degrees C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times of background, preferably 10 times of background hybridization. Exemplary stringent hybridization conditions include the following: 50% formamide, 5×SSC, and 1% SDS, incubating at 42 degrees C., or, 5×SSC, 1% SDS, incubating at 65 degrees C., with wash in 0.2×SSC, and 0.1% SDS at 50 degrees C.

In the context of the present invention, a condition of hybridization for isolating a DNA encoding a polypeptide functionally equivalent to the human PRMT1 protein can be routinely selected by a person skilled in the art. For example, hybridization may be performed by conducting pre-hybridization at 68 degrees C. for 30 min or longer using "Rapid-hyb buffer" (Amersham LIFE SCIENCE), adding a labeled probe, and warming at 68 degrees C. for 1 hour or longer. The following washing step can be conducted, for example, in a low stringent condition. An exemplary low stringent condition may include 42 degrees C., 2×SSC, 0.1% SDS, preferably 50 degrees C., 2×SSC, 0.1% SDS. High stringency conditions are often preferably used. An exemplary high stringency condition may include washing 3 times in 2×SSC, 0.01% SDS at room temperature for 20 min, then washing 3 times in 1×SSC, 0.1% SDS at 37 degrees C. for 20 min, and washing twice in 1×SSC, 0.1% SDS at 50 degrees C. for 20 min. However, several factors, such as temperature and salt concentration, can influence the stringency of hybridization and one skilled in the art can suitably select the factors to achieve the requisite stringency.

Generally, it is known that modifications of one or more amino acid in a protein do not influence the function of the protein. In fact, mutated or modified proteins, proteins having amino acid sequences modified by substituting, deleting, inserting, and/or adding one or more amino acid residues of a certain amino acid sequence, have been known to retain the original biological activity (Mark et al., Proc Natl Acad Sci USA 81: 5662-6 (1984); Zoller and Smith, Nucleic Acids Res 10:6487-500 (1982); Dalbadie-McFarland et al., Proc Natl Acad Sci USA 79: 6409-13 (1982)). Accordingly, one of skill in the art will recognize that individual additions, deletions, insertions, or substitutions to an amino acid sequence which alter a single amino acid or a small percentage of amino acids or those considered to be a "conservative modifications", wherein the alteration of a protein results in a protein with similar functions, are acceptable in the context of the instant invention.

So long as the activity of the protein is maintained, the number of amino acid mutations is not particularly limited. However, it is generally preferred to alter 5% or less of the amino acid sequence. Accordingly, in a preferred embodiment, the number of amino acids to be mutated in such a mutant is generally 30 amino acids or fewer, preferably 20 amino acids or fewer, more preferably 10 amino acids or fewer, more preferably 6 amino acids or fewer, and even more preferably 3 amino acids or fewer.

An amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Conservative substitution tables providing functionally similar amino acids are well known in the art. For example, the following eight groups each contain amino acids that are conservative substitutions for one another:

1) Alanine (A), Glycine (G);
2) Aspartic acid (D), Glutamic acid (E);
3) Aspargine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cystein (C), Methionine (M) (see, e.g., Creighton, Proteins 1984).

Such conservatively modified polypeptides are included in the present PRMT1 protein. However, the present invention is not restricted thereto and the PRMT1 protein includes non-conservative modifications, so long as at least one biological activity of the PRMT1 protein is retained. Furthermore, the modified proteins do not exclude polymorphic variants, inter-species homologues, and those encoded by alleles of these proteins.

Moreover, the PRMT1 gene of the present invention encompasses polynucleotides that encode such functional equivalents of the PRMT1 protein. In addition to hybridization, a gene amplification method, for example, the polymerase chain reaction (PCR) method, can be utilized to isolate a polynucleotide encoding a polypeptide functionally equivalent to the PRMT1 protein, using a primer synthesized based on the sequence information of the protein encoding DNA (SEQ ID NO: 1). Polynucleotides and polypeptides that are functionally equivalent to the human PRMT1 gene and protein, respectively, normally have a high homology to the originating nucleotide or amino acid sequence thereof. "High homology" typically refers to a homology of 40% or higher, preferably 60% or higher, more preferably 80% or higher, even more preferably 90% to 95% or higher. The homology of a particular polynucleotide or polypeptide can be determined by following the algorithm in "Wilbur and Lipman, Proc Natl Acad Sci USA 80: 726-30 (1983)".

A Method for Diagnosing Cancer:

The expression of PRMT1 was found to be specifically elevated in bladder cancer, gastric cancer, colorectal cancer, breast cancer, esophageal cancer, lung cancer, lymphoma, pancreatic cancer and testicular cancer (FIG. 1 and table 3). Therefore, PRMT1 genes identified herein as well as their transcription and translation products find diagnostic utility as a marker for cancers such as bladder cancer, gastric cancer, colorectal cancer, breast cancer, esophageal cancer, lung cancer, lymphoma, pancreatic cancer and testicular cancer, and by measuring the expression of PRMT1 in a sample. Those cancers can be diagnosed or detected by comparing the expression level of PRMT1 between a subject-derived sample with a normal sample. Specifically, the present invention provides a method for diagnosing or detecting cancers by determining the expression level of PRMT1 in the subject. In this present invention, cancer indicates bladder cancer, gastric cancer, colorectal cancer, breast cancer, esophageal cancer, lung cancer, lymphoma, pancreatic cancer and testicular cancer, and lung cancers that can be diagnosed by the present method include NSCLC and SCLC. Furthermore, NSCLC, including lung adenocarcinoma and lung squamous cell carcinoma (SCC), can also be diagnosed or detected by the present invention.

Alternatively, the present invention provides a method for detecting or identifying cancer cells in a subject-derived pancreatic tissue sample, said method comprising the step of determining the expression level of the PRMT1 gene in a subject-derived biological sample, wherein an increase in said expression level as compared to a normal control level of said gene indicates the presence or suspicion of cancer cells in the tissue.

According to the present invention, an intermediate result for examining the condition of a subject may be provided. Such intermediate result may be combined with additional information to assist a doctor, nurse, or other practitioner to diagnose that a subject suffers from the disease. Alternatively, the present invention may be used to detect cancerous cells in a subject-derived tissue, and provide a doctor with useful information to diagnose that the subject suffers from the disease.

For example, according to the present invention, when there is doubt regarding the presence of cancer cells in the tissue obtained from a subject, clinical decisions can be reached by considering the expression level of the PRMT1 gene, plus a different aspect of the disease including tissue pathology, levels of known tumor marker(s) in blood, and clinical course of the subject, etc. For example, some well-known diagnostic pancreatic cancer markers in blood include ACT, AFP, BCA225, BFP, CA15-3, CA19-9, CA50, CA72-4, CA125, CA130, CA602, CEA, DUPAN-2, IAP, KMO-1, alpha-macrogloblin, NCC-ST-439, NSE, PIVKA-II, SCC, sICAM-1, SLX, SP1, SOD, Span-1, STN, TK activity, TPA, YH-206, elastase I, cytokeratin-19 fragment, and CYFRA21-

1. Namely, in this particular embodiment of the present invention, the outcome of the gene expression analysis serves as an intermediate result for further diagnosis of a subject's disease state.

Specifically, the present invention provides the following methods [1] to [10]:

[1] A method of detecting or diagnosing cancer in a subject, comprising determining a expression level of PRMT1 in the subject derived biological sample, wherein an increase of said level compared to a normal control level of said gene indicates that said subject suffers from or is at risk of developing cancer.

[2] The method of [1], wherein the expression level is at least 10% greater than the normal control level.

[3] The method of [1], wherein the expression level is detected by a method selected from among:
   (a) detecting an mRNA including the sequence of PRMT1,
   (b) detecting a protein including the amino acid sequence of PRMT1, and
   (c) detecting a biological activity of a protein including the amino acid sequence of PRMT1.

[4] The method of [1], wherein the cancer is bladder cancer, gastric cancer, colorectal cancer, breast cancer, esophageal cancer, lung cancer, lymphoma, pancreatic cancer and testicular cancer.

[5] The method of [3], wherein the expression level is determined by detecting hybridization of a probe to a gene transcript of the gene.

[6] The method of [3], wherein the expression level is determined by detecting the binding of an antibody against the protein encoded by a gene as the expression level of the gene.

[7] The method of [1], wherein the biological sample includes biopsy, sputum or blood.

[8] The method of [1], wherein the subject-derived biological sample includes an epithelial cell.

[9] The method of [1], wherein the subject-derived biological sample includes a cancer cell.

[10] The method of [1], wherein the subject-derived biological sample includes a cancerous epithelial cell.

The method of diagnosing cancer will be described in more detail below.

A subject to be diagnosed by the present method is preferably a mammal. Exemplary mammals include, but are not limited to, e.g., human, non-human primate, mouse, rat, dog, cat, horse, and cow.

It is preferred to collect a biological sample from the subject to be diagnosed to perform the diagnosis. Any biological material can be used as the biological sample for the determination so long as it includes the objective transcription or translation product of PRMT1. The biological samples include, but are not limited to, bodily tissues which are desired for diagnosing or are suspicion of suffering from cancer, and fluids, such as biopsy, blood, sputum and urine. Preferably, the biological sample contains a cell population comprising an epithelial cell, more preferably a cancerous epithelial cell or an epithelial cell derived from tissue suspected to be cancerous. Further, if necessary, the cell may be purified from the obtained bodily tissues and fluids, and then used as the biological sample.

According to the present invention, the expression level of PRMT1 in the subject-derived biological sample is determined. The expression level can be determined at the transcription (nucleic acid) product level, using methods known in the art. For example, the mRNA of PRMT1 may be quantified using probes by hybridization methods (e.g., Northern hybridization). The detection may be carried out on a chip or an array. The use of an array is preferable for detecting the expression level of a plurality of genes (e.g., various cancer specific genes) including PRMT1. Those skilled in the art can prepare such probes utilizing the sequence information of PRMT1. For example, the cDNA of PRMT1 may be used as the probes. If necessary, the probe may be labeled with a suitable label, such as dyes, fluorescent and isotopes, and the expression level of the gene may be detected as the intensity of the hybridized labels.

Furthermore, the transcription product of PRMT1 may be quantified using primers by amplification-based detection methods (e.g., RT-PCR). Such primers can also be prepared based on the available sequence information of the gene. For example, the primers (SEQ ID NO 7 and 8, or 9 and 10) used in the Example may be employed for the detection by RT-PCR or Northern blot, but the present invention is not restricted thereto.

Specifically, a probe or primer used for the present method hybridizes under stringent, moderately stringent, or low stringent conditions to the mRNA of PRMT1. As used herein, the phrase "stringent (hybridization) conditions" refers to conditions under which a probe or primer will hybridize to its target sequence, but to no other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing agents, such as formamide.

Alternatively, the translation product may be detected for the diagnosis of the present invention. For example, the quantity of PRMT1 protein may be determined. A method for determining the quantity of the protein as the translation product includes immunoassay methods that use an antibody specifically recognizing the protein. The antibody may be monoclonal or polyclonal. Furthermore, any fragment or modification (e.g., chimeric antibody, scFv, Fab, F(ab')2, Fv, etc.) of the antibody may be used for the detection, so long as the fragment retains the binding ability to PRMT1 protein. Methods to prepare these kinds of antibodies for the detection of proteins are well known in the art, and any method may be employed in the present invention to prepare such antibodies and equivalents thereof.

As another method to detect the expression level of PRMT1 gene based on its translation product, the intensity of staining may be observed via immunohistochemical analysis using an antibody against PRMT1 protein. Namely, the observation of strong staining indicates increased presence of the protein and at the same time high expression level of PRMT1 gene.

Moreover, in addition to the expression level of PRMT1 gene, the expression level of other cancer-associated genes, for example, genes known to be differentially expressed in cancer may also be determined to improve the accuracy of the diagnosis.

The expression level of cancer marker gene including PRMT1 gene in a biological sample can be considered to be increased if it increases from the control level of the corresponding cancer marker gene by, for example, 10%, 25%, or 50%; or increases to more than 1.1 fold, more than 1.5 fold, more than 2.0 fold, more than 5.0 fold, more than 10.0 fold, or more.

The control level may be determined at the same time with the test biological sample by using a sample(s) previously collected and stored from a subject/subjects whose disease state (cancerous or non-cancerous) is/are known. Alternatively, the control level may be determined by a statistical method based on the results obtained by analyzing previously determined expression level(s) of PRMT1 gene in samples from subjects whose disease state are known. Furthermore, the control level can be a database of expression patterns from previously tested cells. Moreover, according to an aspect of the present invention, the expression level of PRMT1 gene in a biological sample may be compared to multiple control levels, which control levels are determined from multiple reference samples. It is preferred to use a control level determined from a reference sample derived from a tissue type similar to that of the subject-derived biological sample. Moreover, it is preferred, to use the standard value of the expression levels of PRMT1 gene in a population with a known disease state. The standard value may be obtained by any method known in the art. For example, a range of mean +/−2 S.D. or mean +/−3 S.D. may be used as standard value.

In the context of the present invention, a control level determined from a biological sample that is known not to be cancerous is referred to as a "normal control level". On the other hand, if the control level is determined from a cancerous biological sample, it is referred to as a "cancerous control level".

When the expression level of PRMT1 gene is increased as compared to the normal control level or is similar to the cancerous control level, the subject may be diagnosed to be suffering from or at a risk of developing cancer. Furthermore, in the case where the expression levels of multiple cancer-related genes are compared, a similarity in the gene expression pattern between the sample and the reference which is cancerous indicates that the subject is suffering from or at a risk of developing cancer.

Difference between the expression levels of a test biological sample and the control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

A Kit for Diagnosing Cancer:

The present invention provides a kit for diagnosing cancer. Preferably, the cancer is bladder cancer, gastric cancer, colorectal cancer, breast cancer, esophageal cancer, lung cancer, lymphoma, pancreatic cancer or testicular cancer. Specifically, the kit includes at least one reagent for detecting the expression of the PRMT1 gene in a subject-derived biological sample, which reagent may be selected from the group of:

(a) a reagent for detecting mRNA of the PRMT1 gene;
(b) a reagent for detecting the PRMT1 protein; and
(c) a reagent for detecting the biological activity of the PRMT1 protein.

Suitable reagents for detecting mRNA of the PRMT1 gene include nucleic acids that specifically bind to or identify the PRMT1 mRNA, such as oligonucleotides which have a complementary sequence to a part of the PRMT1 mRNA. These kinds of oligonucleotides are exemplified by primers and probes that are specific to the PRMT1 mRNA. These kinds of oligonucleotides may be prepared based on methods well known in the art. If needed, the reagent for detecting the PRMT1 mRNA may be immobilized on a solid matrix. Moreover, more than one reagent for detecting the PRMT1 mRNA may be included in the kit.

On the other hand, suitable reagents for detecting the PRMT1 protein include antibodies to the PRMT1 protein. The antibody may be monoclonal or polyclonal. Furthermore, any fragment or modification (e.g., chimeric antibody, scFv, Fab, F(ab')2, Fv, etc.) of the antibody may be used as the reagent, so long as the fragment retains the binding ability to the PRMT1 protein. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of antibodies to their targets are well known in the art and any labels and methods may be employed for the present invention. Moreover, more than one reagent for detecting the PRMT1 protein may be included in the kit.

Furthermore, the biological activity can be determined by, for example, measuring the cell proliferating activity due to the expressed PRMT1 protein in the biological sample. For example, the cell is cultured in the presence of a subject-derived biological sample, and then by detecting the speed of proliferation, or by measuring the cell cycle or the colony forming ability the cell proliferating activity of the biological sample can be determined. If needed, the reagent for detecting the PRMT1 mRNA may be immobilized on a solid matrix. Moreover, more than one reagent for detecting the biological activity of the PRMT1 protein may be included in the kit.

The kit may contain more than one of the aforementioned reagents. Furthermore, the kit may include a solid matrix and reagent for binding a probe against the PRMT1 gene or antibody against the PRMT1 protein, a medium and container for culturing cells, positive and negative control reagents, and a secondary antibody for detecting an antibody against the PRMT1 protein. For example, tissue samples obtained from subject suffering from cancer or not may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be comprised in a container with a label. Suitable containers include bottles, vials, and test tubes. The containers may be formed from a variety of materials, such as glass or plastic.

As an embodiment of the present invention, when the reagent is a probe against the PRMT1 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of PRMT1 mRNA present in the sample. The detection sites may be configured in any suitably detectable shape and are typically in the shape of a bar or dot spanning the width of a test strip.

The kit of the present invention may further include a positive control sample or PRMT1 standard sample. The positive control sample of the present invention may be prepared by collecting PRMT1 positive samples and then those PRMT1 level are assayed. The PRMT1 level of the positive control sample is, for example more than cut off value.

Screening for an Anti-Cancer Compound:

In the context of the present invention, agents to be identified through the present screening methods may be any compound or composition including several compounds. Furthermore, the test agent exposed to a cell or protein according to the screening methods of the present invention may be a single compound or a combination of compounds. When a combination of compounds is used in the methods, the compounds may be contacted sequentially or simultaneously.

Any test agent, for example, cell extracts, cell culture supernatant, products of fermenting microorganism, extracts from marine organism, plant extracts, purified or crude proteins, peptides, non-peptide compounds, synthetic micromolecular compounds (including nucleic acid constructs, such as anti-sense RNA, siRNA, Ribozymes, and aptamer etc.) and natural compounds can be used in the screening methods of the present invention. The test agent of the present invention can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam, Anticancer Drug Des 1997, 12: 145-67). Examples of methods for the synthesis of molecular libraries can be found in the art (DeWitt et al., Proc Natl Acad Sci USA 1993, 90: 6909-13; Erb et al., Proc Natl Acad Sci USA 1994, 91: 11422-6; Zuckermann et al., J Med Chem 37: 2678-85, 1994; Cho et al., Science 1993, 261: 1303-5; Carell et al., Angew Chem Int Ed Engl 1994, 33: 2059; Carell et al., Angew Chem Int Ed Engl 1994, 33: 2061; Gallop et al., J Med Chem 1994, 37: 1233-51). Libraries of compounds may be presented in solution (see Houghten, Bio/Techniques 1992, 13: 412-21) or on beads (Lam, Nature 1991, 354: 82-4), chips (Fodor, Nature 1993, 364: 555-6), bacteria (U.S. Pat. No. 5,223,409), spores (U.S. Pat. Nos. 5,571,698; 5,403,484, and 5,223,409), plasmids (Cull et al., Proc Natl Acad Sci USA 1992, 89: 1865-9) or phage (Scott and Smith, Science 1990, 249: 386-90; Devlin, Science 1990, 249: 404-6; Cwirla et al., Proc Natl Acad Sci USA 1990, 87: 6378-82; Felici, J Mol Biol 1991, 222: 301-10; US Pat. Application 2002103360).

A compound in which a part of the structure of the compound screened by any of the present screening methods is converted by addition, deletion and/or replacement, is included in the agents obtained by the screening methods of the present invention.

Furthermore, when the screened test agent is a protein, for obtaining a DNA encoding the protein, either the whole amino acid sequence of the protein may be determined to deduce the nucleic acid sequence coding for the protein, or partial amino acid sequence of the obtained protein may be analyzed to prepare an oligo DNA as a probe based on the sequence, and screen cDNA libraries with the probe to obtain a DNA encoding the protein. The obtained DNA is confirmed it's usefulness in preparing the test agent which is a candidate for treating or preventing cancer.

Test agents useful in the screenings described herein can also be antibodies that specifically bind to PRMT1 protein or partial peptides thereof that lack the biological activity of the original proteins in vivo.

Although the construction of test agent libraries is well known in the art, herein below, additional guidance in identifying test agents and construction libraries of such agents for the present screening methods are provided.

(i) Molecular Modeling:

Construction of test agent libraries is facilitated by knowledge of the molecular structure of compounds known to have the properties sought, and/or the molecular structure of PRMT1. One approach to preliminary screening of test agents suitable for further evaluation is computer modeling of the interaction between the test agent and its target.

Computer modeling technology allows the visualization of the three-dimensional atomic structure of a selected molecule and the rational design of new compounds that will interact with the molecule. The three-dimensional construct typically depends on data from x-ray crystallographic analysis or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menudriven interfaces between the molecular design program and the user.

An example of the molecular modeling system described generally above includes the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen et al. Acta Pharmaceutica Fennica 1988, 97: 159-66; Ripka, New Scientist 1988, 54-8; McKinlay & Rossmann, Annu Rev Pharmacol Toxiciol 1989, 29: 111-22; Perry & Davies, Prog Clin Biol Res 1989, 291: 189-93; Lewis & Dean, Proc R Soc Lond 1989, 236: 125-40, 141-62; and, with respect to a model receptor for nucleic acid components, Askew et al., J Am Chem Soc 1989, 111: 1082-90.

Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. See, e.g., DesJarlais et al., Med Chem 1988, 31: 722-9; Meng et al., J Computer Chem 1992, 13: 505-24; Meng et al., Proteins 1993, 17: 266-78; Shoichet et al., Science 1993, 259: 1445-50.

Once a putative inhibitor has been identified, combinatorial chemistry techniques can be employed to construct any number of variants based on the chemical structure of the identified putative inhibitor, as detailed below. The resulting library of putative inhibitors, or "test agents" may be screened using the methods of the present invention to identify test agents treating or preventing a cancer, such as bladder cancer, gastric cancer, colorectal cancer, breast cancer, esophageal cancer, lung cancer, lymphoma, pancreatic cancer and testicular cancer.

(ii) Combinatorial Chemical Synthesis:

Combinatorial libraries of test agents may be produced as part of a rational drug design program involving knowledge of core structures existing in known inhibitors. This approach allows the library to be maintained at a reasonable size, facilitating high throughput screening. Alternatively, simple, particularly short, polymeric molecular libraries may be constructed by simply synthesizing all permutations of the molecular family making up the library. An example of this latter approach would be a library of all peptides six amino acids in length. Such a peptide library could include every 6 amino acid sequence permutation. This type of library is termed a linear combinatorial chemical library.

Preparation of Combinatorial Chemical Libraries is Well Known to Those of Skill in the art, and may be generated by either chemical or biological synthesis. Combinatorial chemical libraries include, but are not limited to, peptide libraries (see, e.g., U.S. Pat. No. 5,010,175; Furka, Int J Pept Prot Res 1991, 37: 487-93; Houghten et al., Nature 1991, 354: 84-6). Other chemistries for generating chemical diversity libraries can also be used. Such chemistries include, but are not limited to: peptides (e.g., PCT Publication No. WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (DeWitt et al., Proc Natl Acad Sci USA 1993, 90:6909-13), vinylogous polypeptides (Hagihara et al., J Amer Chem Soc 1992, 114: 6568), non-peptidal peptidomimetics with glucose scaffolding (Hirschmann et al., J Amer Chem Soc 1992, 114: 9217-8), analogous organic syntheses of small compound libraries (Chen et al., J. Amer Chem Soc 1994, 116: 2661), oligocarbamates (Cho et al., Science 1993, 261: 1303), and/or peptidylphosphonates (Campbell et al., J Org Chem 1994, 59: 658), nucleic acid libraries (see Ausubel, Current Protocols in Molecular Biology 1995 supplement; Sambrook et al., Molecular Cloning: A Laboratory Manual, 1989, Cold Spring Harbor Laboratory, New York, USA), peptide nucleic acid libraries (see, e.g., U.S. Pat. No. 5,539,083), antibody libraries (see, e.g., Vaughan et al., Nature Biotechnology 1996, 14(3):309-14 and PCT/US96/10287), carbohydrate libraries (see, e.g., Liang et al., Science 1996, 274: 1520-22; U.S. Pat. No. 5,593,853), and small organic molecule libraries (see, e.g., benzodiazepines, Gordon EM. Curr Opin Biotechnol. 1995 Dec. 1; 6(6):624-31; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

(iii) Other Candidates:

Another approach uses recombinant bacteriophage to produce libraries. Using the "phage method" (Scott & Smith, Science 1990, 249: 386-90; Cwirla et al., Proc Natl Acad Sci USA 1990, 87: 6378-82; Devlin et al., Science 1990, 249: 404-6), very large libraries can be constructed (e.g., 106-108 chemical entities). A second approach uses primarily chemical methods, of which the Geysen method (Geysen et al., Molecular Immunology 1986, 23: 709-15; Geysen et al., J Immunologic Method 1987, 102: 259-74); and the method of Fodor et al. (Science 1991, 251: 767-73) are examples. Furka et al. (14th International Congress of Biochemistry 1988, Volume #5, Abstract FR:013; Furka, Int J Peptide Protein Res 1991, 37: 487-93), Houghten (U.S. Pat. No. 4,631,211) and Rutter et al. (U.S. Pat. No. 5,010,175) describe methods to produce a mixture of peptides that can be tested as agonists or antagonists.

Aptamers are macromolecules composed of nucleic acid that bind tightly to a specific molecular target. Tuerk and Gold (Science. 249:505-510 (1990)) discloses SELEX (Systematic Evolution of Ligands by Exponential Enrichment) method for selection of aptamers. In the SELEX method, a large library of nucleic acid molecules {e.g., $10^{15}$ different molecules) can be used for screening.

Screening for a PRMT1 Binding Compound:

In present invention, over-expression of PRMT1 was detected in bladder cancer, gastric cancer, colorectal cancer, breast cancer, esophageal cancer, lung cancer, lymphoma, pancreatic cancer and testicular cancer, in spite of no expression in normal organs (FIG. 1, 2 and Table 3). Therefore, using the PRMT1 genes and proteins encoded by the genes, the present invention provides a method of screening for a compound that binds to PRMT1. Due to the expression of PRMT1 in cancer, a compound binds to PRMT1 is expected to suppress the proliferation of cancer cells, and thus be useful for treating or preventing cancer. Therefore, the present invention also provides a method for screening a compound that suppresses the proliferation of cancer cells, and a method for screening a compound for treating or preventing cancer using the PRMT1 polypeptide. Specially, an embodiment of this screening method includes the steps of:

(a) contacting a test compound with a polypeptide encoded by a polynucleotide of PRMT1;

(b) detecting the binding activity between the polypeptide and the test compound; and (c) selecting the test compound that binds to the polypeptide.

The method of the present invention will be described in more detail below.

The PRMT1 polypeptide to be used for screening may be a recombinant polypeptide or a protein derived from the nature or a partial peptide thereof. The polypeptide to be contacted with a test compound can be, for example, a purified polypeptide, a soluble protein, a form bound to a carrier or a fusion protein fused with other polypeptides.

As a method of screening for proteins, for example, that bind to the PRMT1 polypeptide using the PRMT1 polypeptide, many methods well known by a person skilled in the art can be used. Such a screening can be conducted by, for example, immunoprecipitation method, specifically, in the following manner. The gene encoding the PRMT1 polypeptide is expressed in host (e.g., animal) cells and so on by inserting the gene to an expression vector for foreign genes, such as pSV2neo, pcDNA I, pcDNA3.1, pCAGGS and pCD8.

The promoter to be used for the expression may be any promoter that can be used commonly and include, for example, the SV40 early promoter (Rigby in Williamson (ed.), Genetic Engineering, vol. 3. Academic Press, London, 83-141 (1982)), the EF-alpha promoter (Kim et al., Gene 91:

217-23 (1990)), the CAG promoter (Niwa et al., Gene 108: 193 (1991)), the RSV LTR promoter (Cullen, Methods in Enzymology 152: 684-704 (1987)) the SR alpha promoter (Takebe et al., Mol Cell Biol 8: 466 (1988)), the CMV immediate early promoter (Seed and Aruffo, Proc Natl Acad Sci USA 84: 3365-9 (1987)), the SV40 late promoter (Gheysen and Fiers, J Mol Appl Genet. 1: 385-94 (1982)), the Adenovirus late promoter (Kaufman et al., Mol Cell Biol 9: 946 (1989)), the HSV TK promoter and so on.

The introduction of the gene into host cells to express a foreign gene can be performed according to any methods, for example, the electroporation method (Chu et al., Nucleic Acids Res 15: 1311-26 (1987)), the calcium phosphate method (Chen and Okayama, Mol Cell Biol 7: 2745-52 (1987)), the DEAE dextran method (Lopata et al., Nucleic Acids Res 12: 5707-17 (1984); Sussman and Milman, Mol Cell Biol 4: 1641-3 (1984)), the Lipofectin method (Derijard B., Cell 76: 1025-37 (1994); Lamb et al., Nature Genetics 5: 22-30 (1993): Rabindran et al., Science 259: 230-4 (1993)) and so on.

The polypeptide encoded by PRMT1 gene can be expressed as a fusion protein including a recognition site (epitope) of a monoclonal antibody by introducing the epitope of the monoclonal antibody, whose specificity has been revealed, to the N- or C-terminus of the polypeptide. A commercially available epitope-antibody system can be used (Experimental Medicine 13: 85-90 (1995)). Vectors which can express a fusion protein with, for example, beta-galactosidase, maltose binding protein, glutathione S-transferase, green florescence protein (GFP) and so on by the use of its multiple cloning sites are commercially available. Also, a fusion protein prepared by introducing only small epitopes consisting of several to a dozen amino acids so as not to change the property of the PRMT1 polypeptide by the fusion is also reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage) and such, and monoclonal antibodies recognizing them can be used as the epitope-antibody system for screening proteins binding to the PRMT1 polypeptide (Experimental Medicine 13: 85-90 (1995)).

In immunoprecipitation, an immune complex is formed by adding these antibodies to cell lysate prepared using an appropriate detergent. The immune complex consists of the PRMT1 polypeptide, a polypeptide including the binding ability with the polypeptide, and an antibody. Immunoprecipitation can be also conducted using antibodies against the PRMT1 polypeptide, besides using antibodies against the above epitopes, which antibodies can be prepared as described above. An immune complex can be precipitated, for example by Protein A sepharose or Protein G sepharose when the antibody is a mouse IgG antibody. If the polypeptide encoded by PRMT1 gene is prepared as a fusion protein with an epitope, such as GST, an immune complex can be formed in the same manner as in the use of the antibody against the PRMT1 polypeptide, using a substance specifically binding to these epitopes, such as glutathione-Sepharose 4B.

Immunoprecipitation can be performed by following or according to, for example, the methods in the literature (Harlow and Lane, Antibodies, 511-52, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the PRMT1 polypeptide is difficult to detect by a common staining method, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein can be purified directly from the SDS-polyacrylamide gel and its sequence can be determined, when the molecular weight of a protein has been revealed.

As a method of screening for proteins binding to the PRMT1 polypeptide using the polypeptide, for example, West-Western blotting analysis (Skolnik et al., Cell 65: 83-90 (1991)) can be used. Specifically, a protein binding to the PRMT1 polypeptide can be obtained by preparing a cDNA library from cultured cells expected to express a protein binding to the PRMT1 polypeptide using a phage vector (e.g., ZAP), expressing the protein on LB-agarose, fixing the protein expressed on a filter, reacting the purified and labeled PRMT1 polypeptide with the above filter, and detecting the plaques expressing proteins bound to the PRMT1 polypeptide according to the label. The PRMT1 polypeptide may be labeled by utilizing the binding between biotin and avidin, or by utilizing an antibody that specifically binds to the PRMT1 polypeptide, or a peptide or polypeptide (for example, GST) that is fused to the PRMT1 polypeptide. Methods using radioisotope or fluorescence and such may be also used.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet. 10: 286-92 (1994)").

In the two-hybrid system, the PRMT1 polypeptide is fused to the SRF-binding region or GAL4-binding region and expressed in yeast cells. A cDNA library is prepared from cells expected to express a protein binding to the PRMT1 polypeptide, such that the library, when expressed, is fused to the VP16 or GAL4 transcriptional activation region. The cDNA library is then introduced into the above yeast cells and the cDNA derived from the library is isolated from the positive clones detected (when a protein binding to the polypeptide of the invention is expressed in yeast cells, the binding of the two activates a reporter gene, making positive clones detectable). A protein encoded by the cDNA can be prepared by introducing the cDNA isolated above to E. coli and expressing the protein. As a reporter gene, for example, Ade2 gene, lacZ gene, CAT gene, luciferase gene and such can be used in addition to the HIS3 gene.

A compound binding to the polypeptide encoded by PRMT1 gene can also be screened using affinity chromatography. For example, the PRMT1 polypeptide may be immobilized on a carrier of an affinity column, and a test compound, containing a protein capable of binding to the polypeptide of the invention, is applied to the column. A test compound herein may be, for example, cell extracts, cell lysates, etc. After loading the test compound, the column is washed, and compounds bound to the polypeptide of the invention can be prepared. When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the PRMT1 polypeptide and a test compound can be observed real-time as a surface plasmon resonance signal, using only a minute amount of polypeptide and without labeling (for example, BIAcore, Pharmacia). Therefore, it is possible to evaluate the binding between the polypeptide of the invention and a test compound using a biosensor such as BIAcore.

The methods of screening for molecules that bind when the immobilized PRMT1 polypeptide is exposed to synthetic chemical compounds, or natural substance banks or a random phage peptide display library, and the methods of screening using high-throughput based on combinatorial chemistry techniques (Wrighton et al., Science 273: 458-64 (1996); Verdine, Nature 384: 11-13 (1996); Hogan, Nature 384: 17-9 (1996)) to isolate not only proteins but chemical compounds that bind to the PRMT1 protein (including agonist and antagonist) are well known to one skilled in the art.

Figure 3:
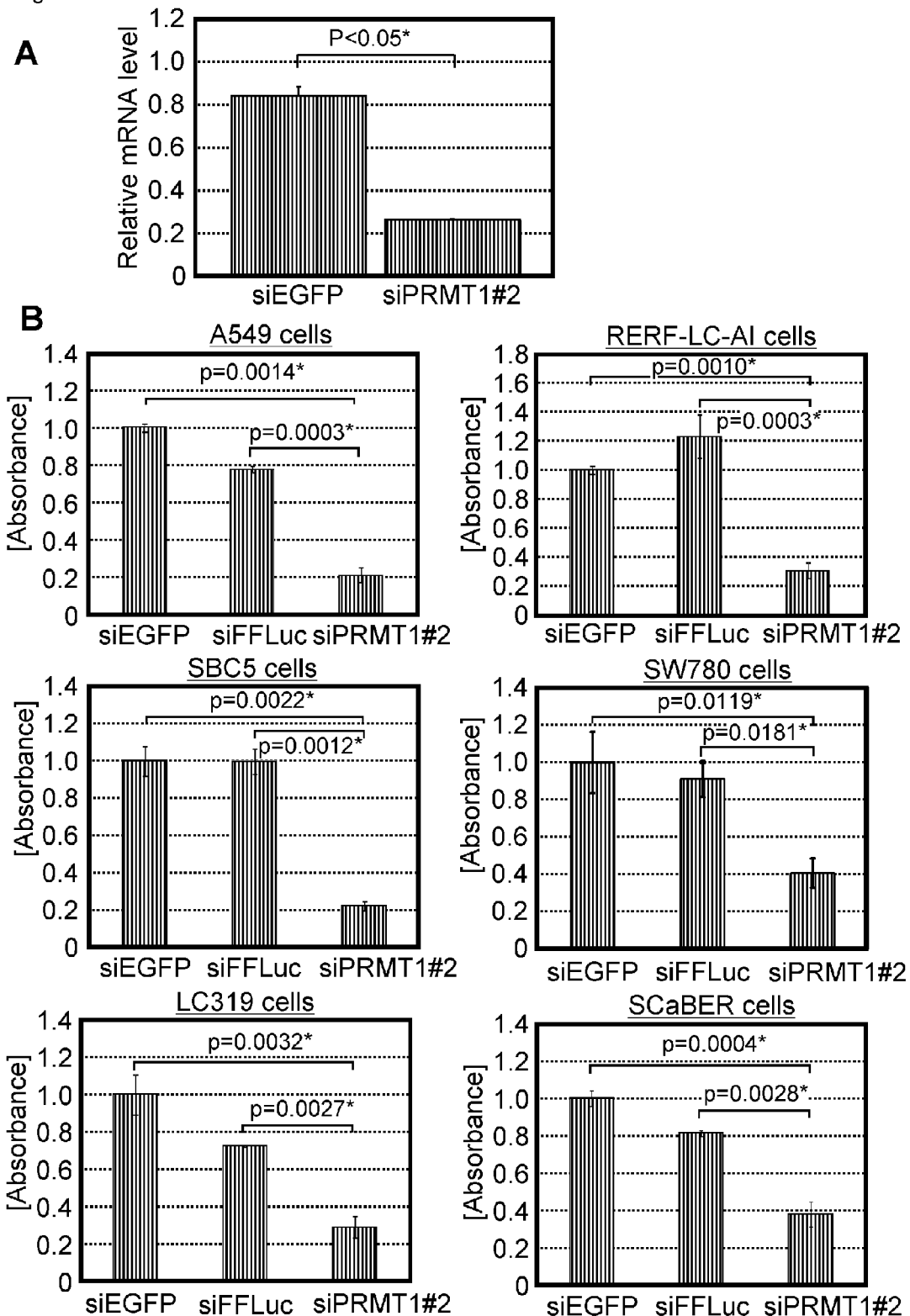
FIG. 3 depicts involvement of PRMT1 in the growth of bladder and lung cancer cells. A, Effect of PRMT1-siRNA (siPRMT1#2) and control siRNA (siEGFP) on PRMT1 expression in SW780 bladder cancer cells. Quantitative RT-PCR was carried out using RNA extracted from cells transfected with siRNA oligonucleotide duplexes. B, Effect of the siRNAs on growth of the lung cancer cells (A549, RERFLC-AI, LC319, SBC5) and bladder cancer cells (SW780, SCaBER) was analyzed by cell counting kit 8.

Screening for a Compound Suppressing the Biological Activity of PRMT1:

In the present invention, the PRMT1 protein has the activity of promoting cell proliferation of cancer cells (FIG. 3). Moreover, arginine methylation of histones and other nuclear proteins is performed by the family of PRMTs (protein arginine methyltransferases). PRMTs use S-adenosylmethionine (SAM)-dependent methylation to modify the guanidino nitrogens of the arginine side chain by adding one or two methyl groups (Bedford M T and Richard S, Mol Cell 2005; 18:263-272). PRMT1 is one of the members of PRMTs family, and also have been demonstrated to have the methyltransferase activity, in particular, an ability to methylate H4/H2A at arginine 3 (Wang H. et al, Science 2001; 293: 853-857). Using these biological activities, the present invention provides a method for screening a compound that suppresses the proliferation of cancer cells expressing PRMT1, and a method for screening a candidate compound for treating or preventing the cancer, such cancer including bladder cancer, gastric cancer, colorectal cancer, breast cancer, esophageal cancer, lung cancer, lymphoma, pancreatic cancer and testicular cancer. Thus, the present invention provides a method of screening for a candidate compound for treating or preventing cancer using the polypeptide encoded by PRMT1 gene including the steps as follows:

(a) contacting a test compound with a polypeptide encoded by a polynucleotide of PRMT1;

(b) detecting a biological activity of the polypeptide of step (a); and (c) selecting the test compound that suppresses the biological activity of the polypeptide encoded by the polynucleotide of PRMT1 as compared to the biological activity of said polypeptide detected in the absence of the test compound.

According to the present invention, the therapeutic effect of the test compound on suppressing the biological activity (e.g., the cell-proliferating activity or the methyltransferase activity) of PRMT1, or a candidate compound for treating or preventing cancer may be evaluated. Therefore, the present invention also provides a method of screening for a candidate compound for suppressing the biological activity of PRMT1, or a candidate compound for treating or preventing cancer, using the PRMT1 polypeptide or fragments thereof, including the following steps:

a) contacting a test compound with the PRMT1 polypeptide or a functional fragment thereof; and b) detecting the biological activity of the polypeptide or fragment of step (a), and c) correlating the biological activity of b) with the therapeutic effect of the test compound.

Such cancer includes bladder cancer, gastric cancer, colorectal cancer, breast cancer, esophageal cancer, lung cancer, lymphoma, pancreatic cancer and testicular cancer. In the present invention, the therapeutic effect may be correlated with the biological activity of the PRMT1 polypeptide or a functional fragment thereof. For example, when the test compound suppresses or inhibits the biological activity of the PRMT1 polypeptide or a functional fragment thereof as compared to a level detected in the absence of the test compound, the test compound may identified or selected as the candidate compound having the therapeutic effect. Alternatively, when the test compound does not suppress or inhibit the biological activity of the PRMT1 polypeptide or a functional fragment thereof as compared to a level detected in the absence of the test compound, the test compound may identified as the agent or compound having no significant therapeutic effect.

The method of the present invention will be described in more detail below.

Any polypeptides can be used for screening so long as they include the biological activity of the PRMT1 protein. Such biological activity includes cell-proliferating activity or methyltransferase activity of the PRMT1 protein. For example, PRMT1 protein can be used and polypeptides functionally equivalent to these proteins can also be used. Such polypeptides may be expressed endogenously or exogenously by cells.

The compound isolated by this screening is a candidate for antagonists of the polypeptide encoded by PRMT1 gene. The term "antagonist" refers to molecules that inhibit the function of the polypeptide by binding thereto. Said term also refers to molecules that reduce or inhibit expression of the gene encoding PRMT1. Moreover, a compound isolated by this screening is a candidate for compounds which inhibit the in vivo interaction of the PRMT1 polypeptide with molecules (including DNAs and proteins).

When the biological activity to be detected in the present method is cell proliferation, it can be detected, for example, by preparing cells which express the PRMT1 polypeptide, culturing the cells in the presence of a test compound, and determining the speed of cell proliferation, measuring the cell cycle and such, as well as by measuring survival cells or the colony forming activity, for example, shown in FIG. 3. The compounds that reduce the speed of proliferation of the cells expressed PRMT1 are selected as candidate compound for treating or preventing cancer.

More specifically, the method includes the step of:

(a) contacting a test compound with cells over-expressing PRMT1;

(b) measuring cell-proliferating activity; and (c) selecting the test compound that reduces the cell-proliferating activity in the comparison with the cell-proliferating activity in the absence of the test compound.

In preferable embodiments, the method of the present invention may further include the steps of:

(d) selecting the test compound that have no effect to the cells no or little expressing PRMT1.

When the biological activity to be detected in the present method is methyltransferase activity, the methyltransferase activity can be determined by contacting a polypeptide with a substrate (e.g., histone H4/H2A or fragments thereof comprising Arginine 3) and a co-factor (e.g., S-adenosyl-L-methionine) under conditions suitable for methylation of the substrate and detecting the methylation level of the substrate.

More specifically, the method includes the step of:

[1] A method of measuring methyl transferase activity of PRMT1, said method comprising the steps of:
(a) contacting a polypeptide encoded by a polynucleotide of PRMT1;
(b) detecting the methylation level of the substrate; and
(c) measuring the methyl transferase activity by correlating the methylation level of the step (b) with the methyl transferase activity.

[2] The method of [1], wherein the substrate is a histone or a fragment thereof comprising at least one methylation region.

[3] The method of [2], wherein the substrate is a histone H4 or H2A or a fragment thereof comprising at least one methylation region.

[4] The method of [3], wherein .the methylarion region is arginine 3.

[4] The method of [1], wherein the cofactor is an S-adenosylmethionine.

[6] The method of [1], wherein the polypeptide is contacted with the substrate and cofactor in the presence of an enhancing agent for the methylation.

[7] The method of [1], wherein the enhancing agent for the methylation is S-adenosyl homocysteine hydrolase (SAHH).

In the present invention, methyltransferase activity of a PRMT1 polypeptide can be determined by methods known in the art. For example, the PRMT1 and a substrate can be incubated with a labeled methyl donor, under suitable assay conditions. A histone H4 or H2A peptides, and S-adenosyl-[methyl-$^{14}$C]-L-methionine, or S-adenosyl-[methyl-$^{3}$H]-L-methionine preferably can be used as the substrate and methyl donor, respectively. Transfer of the radiolabel to the histone H4 or H2A peptides can be detected, for example, by SDS-PAGE electrophoresis and fluorography. Alternatively, following the reaction the histone H4 or H2A peptides can be separated from the methyl donor by filtration, and the amount of radiolabel retained on the filter quantitated by scintillation counting. Other suitable labels that can be attached to methyl donors, such as chromogenic and fluorescent labels, and methods of detecting transfer of these labels to histones and histone peptides, are known in the art.

Alternatively, the methyltransferase activity of PRMT1 can be determined using an unlabeled methyl donor (e.g. S-adenosyl-L-methionine) and reagents that selectively recognize methylated histones or histone peptides. For example, after incubation of the PRMT1, substrate to be methylated and methyl donor, under the condition capable of methylation of the substrate, methylated substrate can be detected by immunological method. Any immunological techniques using an antibody recognizing methylated substrate can be used for the detection. For example, an antibody against methylated histone is commercially available (abcam Ltd.). ELISA or Immunoblotting with antibodies recognizing methylated histone can be used for the present invention.

In the present invention, an agent enhancing the methylation of the substance can be used. SAHH or functional equivalent thereof are one of the preferable enhancing agent for the methylation. The agent enhances the methylation of the substance, the methyltransferase activity can be determined with higher sensitivity thereby. PRMT1 may be contacted with substrate and cofactor under the existence of the enhancing agent.

Furthermore, the present method detecting methyltransferase activity can be performed by preparing cells which express the PRMT1 polypeptide, culturing the cells in the presence of a test compound, and determining methylation level of a histone, for example, by using the antibody specific binding to methylation region.

More specifically, the method includes the step of:
[1] contacting a test compound with cells expressing PRMT1;
[2] detecting a methylation level of histone H4 or H2A arginine 3; and
[3] selecting the test compound that reduces the methylation level in the comparison with the methylation level in the absence of the test compound.

"Suppress the biological activity" as defined herein are preferably at least 10% suppression of the biological activity of PRMT1 in comparison with in absence of the compound, more preferably at least 25%, 50% or 75% suppression and most preferably at 90% suppression.

Screening for a Compound Altering the Expression of PRMT1:

In the present invention, the decrease of the expression of PRMT1 by siRNA causes inhibiting cancer cell proliferation (FIG. 3 and Table 4). Therefore, the present invention provides a method of screening for a compound that inhibits the expression of PRMT1. A compound that inhibits the expression of PRMT1 is expected to suppress the proliferation of cancer cells, and thus is useful for treating or preventing cancer, such cancer including bladder cancer, gastric cancer, colorectal cancer, breast cancer, esophageal cancer, lung cancer, lymphoma, pancreatic cancer and testicular cancer. Therefore, the present invention also provides a method for screening a compound that suppresses the proliferation of cancer cells, and a method for screening a compound for treating or preventing cancer. In the context of the present invention, such screening may include, for example, the following steps:
(a) contacting a candidate compound with a cell expressing PRMT1; and
(b) selecting the candidate compound that reduces the expression level of PRMT1 as compared to a control.

The method of the present invention will be described in more detail below.

Cells expressing the PRMT1 include, for example, cell lines established from bladder cancer, gastric cancer, colorectal cancer, breast cancer, esophageal cancer, lung cancer, lymphoma, pancreatic cancer or testicular cancer; such cells can be used for the above screening of the present invention. The expression level can be estimated by methods well known to one skilled in the art, for example, RT-PCR, Northern blot assay, Western blot assay, immunostaining and flow cytometry analysis. "Reduce the expression level" as defined herein are preferably at least 10% reduction of expression level of PRMT1 in comparison to the expression level in absence of the compound, more preferably at least 25%, 50% or 75% reduced level and most preferably at least 95% reduced level. The compound herein includes chemical compounds, double-strand nucleotides, and so on. The preparation of the double-strand nucleotides is in aforementioned description. In the method of screening, a compound that reduces the expression level of PRMT1 can be selected as candidate compounds to be used for the treatment or prevention of cancer.

Alternatively, the screening method of the present invention may include the following steps:
(a) contacting a candidate compound with a cell into which a vector, including the transcriptional regulatory region of PRMT1 and a reporter gene that is expressed under the control of the transcriptional regulatory region, has been introduced;

(b) measuring the expression or activity of said reporter gene; and (c) selecting the candidate compound that reduces the expression or activity of said reporter gene.

Suitable reporter genes and host cells are well known in the art. For example, reporter genes are luciferase, green florescence protein (GFP), Discosoma sp. Red Fluorescent Protein (DsRed), Chrolamphenicol Acetyltransferase (CAT), lacZ and beta-glucuronidase (GUS), and host cell is COS7, HEK293, HeLa and so on. The reporter construct required for the screening can be prepared by connecting reporter gene sequence to the transcriptional regulatory region of PRMT1. The transcriptional regulatory region of PRMT1 herein is the region from transcription stat site to at least 500 bp upstream, preferably 1000 bp, more preferably 5000 or 10000 bp upstream. A nucleotide segment containing the transcriptional regulatory region can be isolated from a genome library or can be propagated by PCR. The reporter construct required for the screening can be prepared by connecting reporter gene sequence to the transcriptional regulatory region of any one of these genes. Methods for identifying a transcriptional regulatory region, and also assay protocol are well known (Molecular Cloning third edition chapter 17, 2001, Cold Springs Harbor Laboratory Press).

The vector containing the said reporter construct is introduced into host cells and the expression or activity of the reporter gene is detected by methods well known in the art (e.g., using luminometer, absorption spectrometer, flow cytometer and so on). "Reduces the expression or activity" as defined herein are preferably at least 10% reduction of the expression or activity of the reporter gene in comparison with in absence of the compound, more preferably at least 25%, 50% or 75% reduction and most preferably at least 95% reduction.

By screening for candidate compounds that (i) bind to the PRMT1 polypeptide; (ii) suppress/reduce the biological activity (e.g., the cell-proliferating activity or the methyltransferase activity) of the PRMT1 polypeptide; or (iii) reduce the expression level of PRMT1, candidate compounds that have the potential to treat or prevent cancers (e.g., bladder cancer, gastric cancer, colorectal cancer, breast cancer, esophageal cancer, lung cancer, lymphoma, pancreatic cancer and testicular cancer) can be identified. Potential of these candidate compounds to treat or prevent cancers may be evaluated by second and/or further screening to identify therapeutic agent for cancers. For example, when a compound that binds to the PRMT1 polypeptide inhibits the above-described activities of cancer, it may be concluded that such a compound has the PRMT1-specific therapeutic effect.

Double Stranded Molecule:

As used herein, the term "isolated double-stranded molecule" refers to a nucleic acid molecule that inhibits expression of a target gene and includes, for example, short interfering RNA (siRNA; e.g., double-stranded ribonucleic acid (dsRNA) or small hairpin RNA (shRNA)) and short interfering DNA/RNA (siD/R-NA; e.g. double-stranded chimera of DNA and RNA (dsD/R-NA) or small hairpin chimera of DNA and RNA (shD/R-NA)).

As use herein, the term "siRNA" refers to a double-stranded RNA molecule which prevents translation of a target mRNA. Standard techniques of introducing siRNA into the cell are used, including those in which DNA is a template from which RNA is transcribed. The siRNA includes an PRMT1 sense nucleic acid sequence (also referred to as "sense strand"), an PRMT1 anti-sense nucleic acid sequence (also referred to as "anti-sense strand") or both. The siRNA may be constructed such that a single transcript has both the sense and complementary anti-sense nucleic acid sequences of the target gene, e.g., a hairpin. The siRNA may either be a dsRNA or shRNA.

As used herein, the term "dsRNA" refers to a construct of two RNA molecules composed of complementary sequences to one another and that have annealed together via the complementary sequences to form a double-stranded RNA molecule. The nucleotide sequence of two strands may include not only the "sense" or "anti-sense" RNAs selected from a protein coding sequence of target gene sequence, but also RNA molecule having a nucleotide sequence selected from non-coding region of the target gene.

The term "shRNA", as used herein, refers to an siRNA having a stem-loop structure, composed of first and second regions complementary to one another, i.e., sense and anti-sense strands. The degree of complementarity and orientation of the regions are sufficient such that base pairing occurs between the regions, the first and second regions are joined by a loop region, the loop results from a lack of base pairing between nucleotides (or nucleotide analogs) within the loop region. The loop region of an shRNA is a single-stranded region intervening between the sense and anti-sense strands and may also be referred to as "intervening single-strand".

As use herein, the term "siD/R-NA" refers to a double-stranded polynucleotide molecule which is composed of both RNA and DNA, and includes hybrids and chimeras of RNA and DNA and prevents translation of a target mRNA. Herein, a hybrid indicates a molecule wherein a polynucleotide composed of DNA and a polynucleotide composed of RNA hybridize to each other to form the double-stranded molecule; whereas a chimera indicates that one or both of the strands composing the double stranded molecule may contain RNA and DNA. Standard techniques of introducing siD/R-NA into the cell are used. The siD/R-NA includes an PRMT1 sense nucleic acid sequence (also referred to as "sense strand"), an PRMT1 anti-sense nucleic acid sequence (also referred to as "anti-sense strand") or both. The siD/R-NA may be constructed such that a single transcript has both the sense and complementary antisense nucleic acid sequences from the target gene, e.g., a hairpin. The siD/R-NA may either be a dsD/R-NA or shD/R-NA.

As used herein, the term "dsD/R-NA" refers to a construct of two molecules composed of complementary sequences to one another and that have annealed together via the complementary sequences to form a double-stranded polynucleotide molecule. The nucleotide sequence of two strands may comprise not only the "sense" or "anti-sense" polynucleotides sequence selected from a protein coding sequence of target gene sequence, but also polynucleotide having a nucleotide sequence selected from non-coding region of the target gene. One or both of the two molecules constructing the dsD/R-NA are composed of both RNA and DNA (chimeric molecule), or alternatively, one of the molecules is composed of RNA and the other is composed of DNA (hybrid double-strand).

The term "shD/R-NA", as used herein, refers to an siD/R-NA having a stem-loop structure, composed of a first and second regions complementary to one another, i.e., sense and anti-sense strands. The degree of complementarity and orientation of the regions are sufficient such that base pairing occurs between the regions, the first and second regions are joined by a loop region, the loop results from a lack of base pairing between nucleotides (or nucleotide analogs) within the loop region. The loop region of an shD/R-NA is a single-stranded region intervening between the sense and anti-sense strands and may also be referred to as "intervening single-strand".

As used herein, an "isolated nucleic acid" is a nucleic acid removed from its original environment (e.g., the natural environment if naturally occurring) and thus, synthetically altered from its natural state. In the present invention, examples of isolated nucleic acid includes DNA, RNA, and derivatives thereof.

A double-stranded molecule against PRMT1, which molecule hybridizes to target mRNA, decreases or inhibits production of PRMT1 protein encoded by PRMT1 gene by associating with the normally single-stranded mRNA transcript of the gene, thereby interfering with translation and thus, inhibiting expression of the protein. As demonstrated herein, the expression of PRMT1 in several cancer cell lines was inhibited by dsRNA (FIG. 3). Therefore the present invention provides isolated double-stranded molecules that are capable of inhibiting the expression of PRMT1 gene when introduced into a cell expressing the gene. The target sequence of double-stranded molecule may be designed by an siRNA design algorithm such as that mentioned below.

PRMT1 target sequence includes, for example, nucleotides SEQ ID NO: 17 (at the position 803-821 nt of SEQ ID NO: 1)

Specifically, the present invention provides the following double-stranded molecules [1] to [18]:

[1] An isolated double-stranded molecule that, when introduced into a cell, inhibits in vivo expression of PRMT1 and cell proliferation, such molecules composed of a sense strand and an anti-sense strand complementary thereto, hybridized to each other to form the double-stranded molecule;

[2] The double-stranded molecule of [1], wherein said double-stranded molecule acts on mRNA, matching a target sequence of SEQ ID NO: 17 (at the position of 803-821 nt of SEQ ID NO: 1);

[3] The double-stranded molecule of [2], wherein the sense strand contains a sequence corresponding to a target sequence of SEQ ID NO: 17;

[4] The double-stranded molecule of [3], having a length of less than about 100 nucleotides;

[5] The double-stranded molecule of [4], having a length of less than about 75 nucleotides;

[6] The double-stranded molecule of [5], having a length of less than about 50 nucleotides;

[7] The double-stranded molecule of [6] having a length of less than about 25 nucleotides;

[8] The double-stranded molecule of [7], having a length of between about 19 and about 25 nucleotides;

[9] The double-stranded molecule of [1], composed of a single polynucleotide having both the sense and anti-sense strands linked by an intervening single-strand;

[10] The double-stranded molecule of [9], having the general formula 5'-[A]-[B]-[A']-3', wherein [A] is the sense strand containing a sequence corresponding to a target sequence of SEQ ID NO: 17 is the intervening single-strand composed of 3 to 23 nucleotides, and [A'] is the anti-sense strand containing a sequence complementary to [A];

[11] The double-stranded molecule of [1], composed of RNA;

[12] The double-stranded molecule of [1], composed of both DNA and RNA;

[13] The double-stranded molecule of [12], wherein the molecule is a hybrid of a DNA polynucleotide and an RNA polynucleotide;

[14] The double-stranded molecule of [13] wherein the sense and the anti-sense strands are composed of DNA and RNA, respectively;

[15] The double-stranded molecule of [12], wherein the molecule is a chimera of DNA and RNA;

[16] The double-stranded molecule of [15], wherein a region flanking to the 3'-end of the anti-sense strand, or both of a region flanking to the 5'-end of sense strand and a region flanking to the 3'-end of anti-sense strand are RNA;

[17] The double-stranded molecule of [16], wherein the flanking region is composed of 9 to 13 nucleotides; and

[18] The double-stranded molecule of [2], wherein the molecule contains 3' overhang;

The double-stranded molecule of the present invention will be described in more detail below.

Methods for designing double-stranded molecules having the ability to inhibit target gene expression in cells are known. (See, for example, U.S. Pat. No. 6,506,559, herein incorporated by reference in its entirety). For example, a computer program for designing siRNAs is available from the Ambion website (http://www.ambion.com/techlib/misc/siRNA_finder.html).

The computer program selects target nucleotide sequences for double-stranded molecules based on the following protocol.

Selection of Target Sites:

1. Beginning with the AUG start codon of the transcript, scan downstream for AA dinucleotide sequences. Record the occurrence of each AA and the 3' adjacent 19 nucleotides as potential siRNA target sites. Tuschl et al. recommend to avoid designing siRNA to the 5' and 3' untranslated regions (UTRs) and regions near the start codon (within 75 bases) as these may be richer in regulatory protein binding sites, and UTR-binding proteins and/or translation initiation complexes may interfere with binding of the siRNA endonuclease complex.

2. Compare the potential target sites to the appropriate genome database (human, mouse, rat, etc.) and eliminate from consideration any target sequences with significant homology to other coding sequences. Basically, BLAST, which can be found on the NCBI server at: www.ncbi.nlm.nih.gov/BLAST/, is used (Altschul S F et al., Nucleic Acids Res 1997 Sep. 1, 25(17): 3389-402).

3. Select qualifying target sequences for synthesis. Selecting several target sequences along the length of the gene to evaluate is typical.

Using the above protocol, the target sequence of the isolated double-stranded molecules of the present invention were designed as SEQ ID NO: 17 for PRMT1 gene, Double-stranded molecules targeting the above-mentioned target sequences were respectively examined for their ability to suppress the growth of cells expressing the target genes. Therefore, the present invention provides double-stranded molecule targeting the sequences of SEQ ID NO: 17 (at the position 803-821 nt of SEQ ID NO: 1) for PRMT1 gene, The double-stranded molecule of the present invention may be directed to a single target PRMT1 gene sequence or may be directed to a plurality of target PRMT1 gene sequences.

A double-stranded molecule of the present invention targeting the above-mentioned targeting sequence of PRMT1 gene include isolated polynucleotide that contain the nucleic acid sequences of target sequences and/or complementary sequences to the target sequence. Example of polynucleotide targeting PRMT1 gene includes that containing the sequence of SEQ ID NO: 17 and/or complementary sequences to these nucleotides; However, the present invention is not limited to this example, and minor modifications in the aforementioned nucleic acid sequences are acceptable so long as the modified molecule retains the ability to suppress the expression of PRMT1 gene. Herein, the phrase "minor modification" as used in connection with a nucleic acid sequence indicates one, two or several substitution, deletion, addition or insertion of nucleic acids to the sequence.

In the context of the present invention, the term "several" as applies to nucleic acid substitutions, deletions, additions and/or insertions may mean 3-7, preferably 3-5, more preferably 3-4, even more preferably 3 nucleic acid residues.

According to the present invention, a double-stranded molecule of the present invention can be tested for its ability using the methods utilized in the Examples. In the Examples herein below, double-stranded molecules composed of sense strands of various portions of mRNA of PRMT1 genes or anti-sense strands complementary thereto were tested in vitro for their ability to decrease production of PRMT1 gene product in cancer cell lines according to standard methods. Furthermore, for example, reduction in PRMT1 gene product in cells contacted with the candidate double-stranded molecule compared to cells cultured in the absence of the candidate molecule can be detected by, e.g. RT-PCR using primers for PRMT1 mRNA mentioned under Example 1 item "Quantitative RT-PCR". Sequences which decrease the production of PRMT1 gene product in in vitro cell-based assays can then be tested for there inhibitory effects on cell growth. Sequences which inhibit cell growth in in vitro cell-based assay can then be tested for their in vivo ability using animals with cancer, e.g. nude mouse xenograft models, to confirm decreased production of PRMT1 product and decreased cancer cell growth.

When the isolated polynucleotide is RNA or derivatives thereof, base "t" should be replaced with "u" in the nucleotide sequences. As used herein, the term "complementary" refers to Watson-Crick or Hoogsteen base pairing between nucleotides units of a polynucleotide, and the term "binding" means the physical or chemical interaction between two polynucleotides. When the polynucleotide includes modified nucleotides and/or non-phosphodiester linkages, these polynucleotides may also bind each other as same manner. Generally, complementary polynucleotide sequences hybridize under appropriate conditions to form stable duplexes containing few or no mismatches. Furthermore, the sense strand and anti-sense strand of the isolated polynucleotide of the present invention can form double-stranded molecule or hairpin loop structure by the hybridization. In a preferred embodiment, such duplexes contain no more than 1 mismatch for every 10 matches. In an especially preferred embodiment, where the strands of the duplex are fully complementary, such duplexes contain no mismatches.

The polynucleotide is preferably less than 1131 nucleotides in length for PRMT1. For example, the polynucleotide is less than 500, 200, 100, 75, 50, or 25 nucleotides in length for all of the genes. The isolated polynucleotides of the present invention are useful for forming double-stranded molecules against PRMT1 gene or preparing template DNAs encoding the double-stranded molecules. When the polynucleotides are used for forming double-stranded molecules, the polynucleotide may be longer than 19 nucleotides, preferably longer than 21 nucleotides, and more preferably has a length of between about 19 and 25 nucleotides. Alternatively, the double-stranded molecules of the present invention may be double-stranded molecules, wherein the sense strand is hybridize with anti-sense strand at the target sequence to form the double-stranded molecule having less than 500, 200, 100, 75, 50 or 25 nucleotides pair in length. Preferably, the double-stranded molecules have between about 19 and about 25 nucleotides pair in length. Further, the sense strand of the double-stranded molecule may preferably include less than 500, 200, 100, 75, 50, 30, 28, 27, 26, 25 nucleotides, more preferably, between about 19 and about 25 nucleotides.

The double-stranded molecules of the invention may contain one or more modified nucleotides and/or non-phosphodiester linkages. Chemical modifications well known in the art are capable of increasing stability, availability, and/or cell uptake of the double-stranded molecule. The skilled person will be aware of other types of chemical modification which may be incorporated into the present molecules (WO03/070744; WO2005/045037). In one embodiment, modifications can be used to provide improved resistance to degradation or improved uptake. Examples of such modifications include, but are not limited to, phosphorothioate linkages, 2'-O-methyl ribonucleotides (especially on the sense strand of a double-stranded molecule), 2'-deoxy-fluoro ribonucleotides, 2'-deoxy ribonucleotides, "universal base" nucleotides, 5'-C— methyl nucleotides, and inverted deoxybasic residue incorporation (US20060122137).

In another embodiment, modifications can be used to enhance the stability or to increase targeting efficiency of the double-stranded molecule. Examples of such modifications include, but are not limited to, chemical cross linking between the two complementary strands of a double-stranded molecule, chemical modification of a 3' or 5' terminus of a strand of a double-stranded molecule, sugar modifications, nucleobase modifications and/or backbone modifications, 2-fluoro modified ribonucleotides and 2'-deoxy ribonucleotides (WO2004/029212). In another embodiment, modifications can be used to increased or decreased affinity for the complementary nucleotides in the target mRNA and/or in the complementary double-stranded molecule strand (WO2005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deaza, 7-alkyl, or 7-alkenyl purine. In another embodiment, when the double-stranded molecule is a double-stranded molecule with a 3' overhang, the 3'-terminal nucleotide overhanging nucleotides may be replaced by deoxyribonucleotides (Elbashir S M et al., Genes Dev 2001 Jan. 15, 15(2): 188-200). For further details, published documents such as US20060234970 are available. The present invention is not limited to these examples and any known chemical modifications may be employed for the double-stranded molecules of the present invention so long as the resulting molecule retains the ability to inhibit the expression of the target gene.

Furthermore, the double-stranded molecules of the present invention may comprise both DNA and RNA, e.g., dsD/R-NA or shD/R-NA. Specifically, a hybrid polynucleotide of a DNA strand and an RNA strand or a DNA-RNA chimera polynucleotide shows increased stability. Mixing of DNA and RNA, i.e., a hybrid type double-stranded molecule composed of a DNA strand (polynucleotide) and an RNA strand (polynucleotide), a chimera type double-stranded molecule containing both DNA and RNA on any or both of the single strands (polynucleotides), or the like may be formed for enhancing stability of the double-stranded molecule.

The hybrid of a DNA strand and an RNA strand may be either where the sense strand is DNA and the anti-sense strand is RNA, or the opposite so long as it can inhibit expression of the target gene when introduced into a cell expressing the gene. Preferably, the sense strand polynucleotide is DNA and the anti-sense strand polynucleotide is RNA. Also, the chimera type double-stranded molecule may be either where both of the sense and anti-sense strands are composed of DNA and RNA, or where any one of the sense and anti-sense strands is composed of DNA and RNA so long as it has an activity to inhibit expression of the target gene when introduced into a cell expressing the gene. In order to enhance stability of the double-stranded molecule, the molecule preferably contains as much DNA as possible, whereas to induce inhibition of the target gene expression, the molecule is required to be RNA within a range to induce sufficient inhibition of the expression.

As a preferred example of the chimera type double-stranded molecule, an upstream partial region (i.e., a region flanking to the target sequence or complementary sequence thereof within the sense or anti-sense strands) of the double-stranded molecule is RNA. Preferably, the upstream partial region indicates the 5' side (5'-end) of the sense strand and the 3' side (3'-end) of the anti-sense strand. Alternatively, regions flanking to 5'-end of sense strand and/or 3'-end of anti-sense strand are referred to upstream partial region. That is, in preferable embodiments, a region flanking to the 3'-end of the anti-sense strand, or both of a region flanking to the 5'-end of sense strand and a region flanking to the 3'-end of anti-sense strand are composed of RNA. For instance, the chimera or hybrid type double-stranded molecule of the present invention include following combinations.

sense strand:

```
5'[---DNA---]-3'

3'-(RNA)-[DNA]-5':
``` antisense strand,
sense strand:

```
5'-(RNA)-[DNA]-3'

3'-(RNA)-[DNA]-5':
``` antisense strand, and
sense strand:

```
5'-(RNA)-[DNA]-3'

3'-(---RNA---)-5':
``` antisense strand.

The upstream partial region preferably is a domain composed of 9 to 13 nucleotides counted from the terminus of the target sequence or complementary sequence thereto within the sense or anti-sense strands of the double-stranded molecules. Moreover, preferred examples of such chimera type double-stranded molecules include those having a strand length of 19 to 21 nucleotides in which at least the upstream half region (5' side region for the sense strand and 3' side region for the anti-sense strand) of the polynucleotide is RNA and the other half is DNA. In such a chimera type double-stranded molecule, the effect to inhibit expression of the target gene is much higher when the entire anti-sense strand is RNA (US20050004064).

In the present invention, the double-stranded molecule may form a hairpin, such as a short hairpin RNA (shRNA) and short hairpin consisting of DNA and RNA (shD/R-NA). The shRNA or shD/R-NA is a sequence of RNA or mixture of RNA and DNA making a tight hairpin turn that can be used to silence gene expression via RNA interference. The shRNA or shD/R-NA comprises the sense target sequence and the anti-sense target sequence on a single strand wherein the sequences are separated by a loop sequence. Generally, the hairpin structure is cleaved by the cellular machinery into dsRNA or dsD/R-NA, which is then bound to the RNA-induced silencing complex (RISC). This complex binds to and cleaves mRNAs which match the target sequence of the dsRNA or dsD/R-NA.

A loop sequence composed of an arbitrary nucleotide sequence can be located between the sense and anti-sense sequence in order to form the hairpin loop structure. Thus, the present invention also provides a double-stranded molecule having the general formula 5'-[A]-[B]-[A']-3', wherein [A] is the sense strand containing a sequence corresponding to a target sequence, [B] is an intervening single-strand and [A'] is the anti-sense strand containing a complementary sequence to [A]. The target sequence may be selected from among, for example, nucleotide of SEQ ID NO: 17 for PRMT1.

The present invention is not limited to these examples, and the target sequence in [A] may be modified sequences from these examples so long as the double-stranded molecule retains the ability to suppress the expression of the targeted PRMT1 gene. The region [A] hybridizes to [A'] to form a loop composed of the region [B]. The intervening single-stranded portion [B], i.e., loop sequence may be preferably 3 to 23 nucleotides in length. The loop sequence, for example, can be selected from among the following sequences (http://www.ambion.com/techlib/tb/tb_506.html). Furthermore, loop sequence consisting of 23 nucleotides also provides active siRNA (Jacque J M et al., Nature 2002 Jul. 25, 418(6896): 435-8, Epub 2002 Jun. 26):

CCC, CCACC, or CCACACC: Jacque J M et al., Nature 2002 Jul. 25, 418(6896): 435-8, Epub 2002 Jun. 26;

UUCG: Lee N S et al., Nat Biotechnol 2002 May, 20(5): 500-5; Fruscoloni P et al., Proc Natl Acad Sci USA 2003 Feb. 18, 100(4): 1639-44, Epub 2003 Feb. 10; and UUCAAGAGA: Dykxhoorn D M et al., Nat Rev Mol Cell Biol 2003 Jun., 4(6): 457-67.

Examples of preferred double-stranded molecules of the present invention having hairpin loop structure are shown below. In the following structure, the loop sequence can be selected from among AUG, CCC, UUCG, CCACC, CTCGAG, AAGCUU, CCACACC, and UUCAAGAGA; however, the present invention is not limited thereto:

```
                                  (for target sequence SEQ ID NO: 17)
GAGUUCACACGCUGCCACA-[B]-UGUGGCAGCGUGUGAACUC.
```

Furthermore, in order to enhance the inhibition activity of the double-stranded molecules, several nucleotides can be added to 3' end of the sense strand and/or antisense strand of the target sequence, as 3' overhangs. The preferred examples of nucleotides constituting a 3' overhang include "t" and "u", but are not limited to. The number of nucleotides to be added is at least 2, generally 2 to 10, preferably 2 to 5. The added nucleotides form single strand at the 3' end of the sense strand and/or anti-sense strand of the double-stranded molecule. In cases where double-stranded molecules consists of a single polynucleotide to form a hairpin loop structure, a 3' overhang sequence may be added to the 3' end of the single polynucleotide.

The method for preparing the double-stranded molecule is not particularly limited though it is preferable to use a chemical synthetic method known in the art. According to the chemical synthesis method, sense and anti-sense single-stranded polynucleotides are separately synthesized and then annealed together via an appropriate method to obtain a double-stranded molecule. Specific example for the annealing includes wherein the synthesized single-stranded polynucleotides are mixed in a molar ratio of preferably at least about 3:7, more preferably about 4:6, and most preferably substantially equimolar amount (i.e., a molar ratio of about 5:5). Next, the mixture is heated to a temperature at which double-stranded molecules dissociate and then is gradually cooled down. The annealed double-stranded polynucleotide can be purified by usually employed methods known in the art. Example of purification methods include methods utilizing agarose gel electrophoresis or wherein remaining single-stranded polynucleotides are optionally removed by, e.g., degradation with appropriate enzyme.

The regulatory sequences flanking PRMT1 sequences may be identical or different, such that their expression can be modulated independently, or in a temporal or spatial manner. The double-stranded molecules can be transcribed intracellularly by cloning PRMT1 gene templates into a vector containing, e.g., a RNA pol III transcription unit from the small nuclear RNA (snRNA) U6 or the human H1 RNA promoter.

Vector Containing a Double-Stranded Molecule of the Present Invention:

Also included in the present invention are vectors containing one or more of the double-stranded molecules described herein, and a cell containing such a vector.

Specifically, the present invention provides the following vector of [1] to [10].

[1] A vector, encoding a double-stranded molecule that, when introduced into a cell, inhibits in vivo expression of PRMT1 and cell proliferation, such molecules composed of a sense strand and an anti-sense strand complementary thereto, hybridized to each other to form the double-stranded molecule.

[2] The vector of [1], encoding the double-stranded molecule acts on mRNA, matching a target sequence of SEQ ID NO: 17 (at the position of 803-821 nt of SEQ ID NO: 1);

[3] The vector of [1], wherein the sense strand contains a sequence corresponding to a target sequence of SEQ ID NO: 17;

[4] The vector of [3], encoding the double-stranded molecule having a length of less than about 100 nucleotides;

[5] The vector of [4], encoding the double-stranded molecule having a length of less than about 75 nucleotides;

[6] The vector of [5], encoding the double-stranded molecule having a length of less than about 50 nucleotides;

[7] The vector of [6] encoding the double-stranded molecule having a length of less than about 25 nucleotides;

[8] The vector of [7], encoding the double-stranded molecule having a length of between about 19 and about 25 nucleotides;

[9] The vector of [1], wherein the double-stranded molecule is composed of a single polynucleotide having both the sense and anti-sense strands linked by an intervening single-strand;

[10] The vector of [9], encoding the double-stranded molecule having the general formula 5'-[A]-[B]-[A']-3', wherein [A] is the sense strand containing a sequence corresponding to a target sequence of SEQ ID NO: 17, [B] is the intervening single-strand composed of 3 to 23 nucleotides, and [A'] is the anti-sense strand containing a sequence complementary to [A];

A vector of the present invention preferably encodes a double-stranded molecule of the present invention in an expressible form. Herein, the phrase "in an expressible form" indicates that the vector, when introduced into a cell, will express the molecule. In a preferred embodiment, the vector includes regulatory elements necessary for expression of the double-stranded molecule. Such vectors of the present invention may be used for producing the present double-stranded molecules, or directly as an active ingredient for treating cancer.

Vectors of the present invention can be produced, for example, by cloning PRMT1 sequence into an expression vector so that regulatory sequences are operatively-linked to PRMT1 sequence in a manner to allow expression (by transcription of the DNA molecule) of both strands (Lee N S et al., Nat Biotechnol 2002 May, 20(5): 500-5). For example, RNA molecule that is the anti-sense to mRNA is transcribed by a first promoter (e.g., a promoter sequence flanking to the 3' end of the cloned DNA) and RNA molecule that is the sense strand to the mRNA is transcribed by a second promoter (e.g., a promoter sequence flanking to the 5' end of the cloned DNA). The sense and anti-sense strands hybridize in vivo to generate a double-stranded molecule constructs for silencing of the gene. Alternatively, two vectors constructs respectively encoding the sense and anti-sense strands of the double-stranded molecule are utilized to respectively express the sense and anti-sense strands and then forming a double-stranded molecule construct. Furthermore, the cloned sequence may encode a construct having a secondary structure (e.g., hairpin); namely, a single transcript of a vector contains both the sense and complementary anti-sense sequences of the target gene.

The vectors of the present invention may also be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The vectors of the present invention include, for example, viral or bacterial vectors. Examples of expression vectors include attenuated viral hosts, such as vaccinia or fowlpox (see, e.g., U.S. Pat. No. 4,722,848). This approach involves the use of vaccinia virus, e.g., as a vector to express nucleotide sequences that encode the double-stranded molecule. Upon introduction into a cell expressing the target gene, the recombinant vaccinia virus expresses the molecule and thereby suppresses the proliferation of the cell. Another example of useable vector includes Bacille Calmette Guerin (BCG). BCG vectors are described in Stover et al., Nature 1991, 351: 456-60. A wide variety of other vectors are useful for therapeutic administration and production of the double-stranded molecules; examples include adeno and adeno-associated virus vectors, retroviral vectors, *Salmonella typhi* vectors, detoxified anthrax toxin vectors, and the like. See, e.g., Shata et al., Mol Med Today 2000, 6: 66-71; Shedlock et al., J Leukoc Biol 2000, 68: 793-806; and Hipp et al., In Vivo 2000, 14: 571-85.

Method of Inhibiting or Reducing Growth of a Cancer Cell or Treating Cancer Using a Double-Stranded Molecule of the Present Invention:

In present invention, dsRNAs for PRMT1 were tested for their ability to inhibit cell growth. The dsRNA for PRMT1 (FIG. 3), effectively knocked down the expression of the gene in several cancer cell lines coincided with suppression of cell proliferation.

Therefore, the present invention provides methods for inhibiting cell growth, i.e., bladder cancer, gastric cancer, colorectal cancer, breast cancer, esophageal cancer, lung cancer, lymphoma, pancreatic cancer and testicular cancer, by inducing dysfunction of PRMT1 gene via inhibiting the expression of PRMT1. PRMT1 gene expression can be inhibited by any of the aforementioned double-stranded molecules of the present invention which specifically target of PRMT1 gene.

Figure 2:
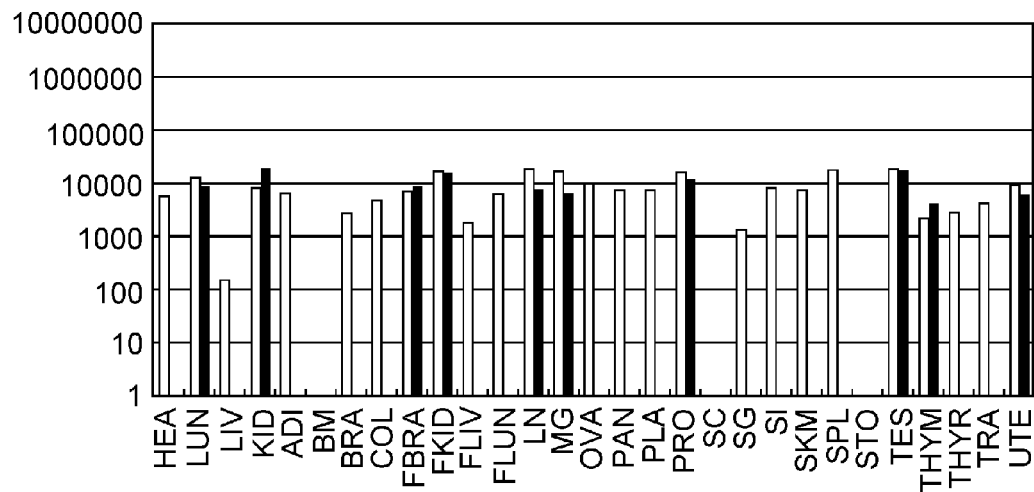
FIG. 2 depicts relative gene expression of PRMT1 in 29 normal tissues based on the cDNA microarray analysis. 12.5 micro g aliquots of poly(A)+ RNA from individual tissues and a mixture of equivalent poly(A)+ RNA from all 29 tissues as a universal control were labeled respectively with Cy5-dCTP and Cy3-dCTP dyes. HEA: Heart, LUN: Lung, LIV: Liver, KID: Kidney, ADI: Mesenteric adipose, BM: Bone Marrow, BRA: Brain, COL: Colon, FBRA: Fetal brain, FKID: Fetal kidney, FLIV: Fetal liver, FLUN: Fetal lung, LN: Lymph node, MG: Mammary gland, OVA: Ovary, PAN: Pancreas, PLA: Placenta, PRO: Prostate, SC: Spinal cord, SG: Spinal ganglion, SI: Small intestine, SKM: Skeletal muscle, SPL: Spleen, STO: Stomach, TES: Testis, THYM: Thymus, THYR: Thyroid, TRA: Trachea, UTE: Uterus
Figure 2:
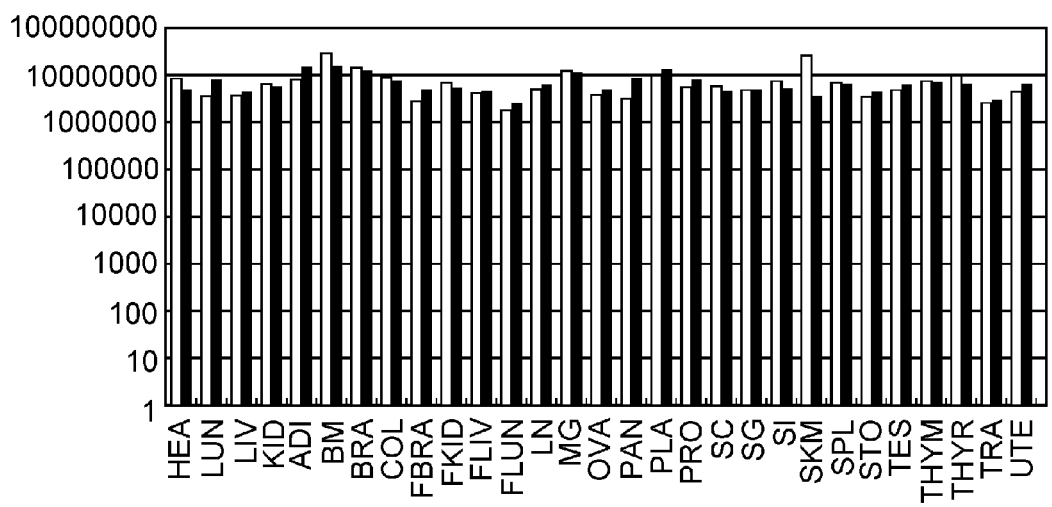

Such ability of the present double-stranded molecules and vectors to inhibit cell growth of cancerous cell indicates that they can be used for methods for treating cancer such as bladder cancer, gastric cancer, colorectal cancer, breast cancer, esophageal cancer, lung cancer, lymphoma, pancreatic cancer and testicular cancer. Thus, the present invention provides methods to treat patients with cancer by administering a double-stranded molecule against PRMT1 gene or a vector expressing the molecule without adverse effect because PRMT1 gene was minimally detected in normal organs (FIG. 2).

Specifically, the present invention provides the following methods [1] to [32]:

[1] A method for inhibiting a growth of cancer cell and treating a cancer, wherein the cancer cell or the cancer expresses a PRMT1 gene, which method includes the step of administering at least one isolated double-stranded molecule inhibiting the expression of PRMT1 in a cell over-expressing the gene and the cell proliferation, wherein the double-stranded molecule is composed of a sense strand and an anti-sense strand complementary thereto, hybridized to each other to form the double-stranded molecule.

[2] The method of [1], wherein the double-stranded molecule acts at mRNA which matches a target sequence of SEQ ID NO: 17 (at the position of 803-821 nt of SEQ ID NO: 13).

[3] The method of [2], wherein the sense strand contains the sequence corresponding to a target sequence of SEQ ID NO: 17.

[4] The method of [1], wherein the cancer to be treated is bladder cancer, gastric cancer, colorectal cancer, breast cancer, esophageal cancer, lung cancer, lymphoma, pancreatic cancer and testicular cancer;

[5] The method of [3], wherein the double-stranded molecule has a length of less than about 100 nucleotides;

[6] The method of [5], wherein the double-stranded molecule has a length of less than about 75 nucleotides;

[7] The method of [6], wherein the double-stranded molecule has a length of less than about 50 nucleotides;

[8] The method of [7], wherein the double-stranded molecule has a length of less than about 25 nucleotides;

[9] The method of [8], wherein the double-stranded molecule has a length of between about 19 and about 25 nucleotides in length;

[10] The method of [1], wherein the double-stranded molecule is composed of a single polynucleotide containing both the sense strand and the anti-sense strand linked by an intervening single-strand;

[11] The method of [10], wherein the double-stranded molecule has the general formula 5'-[A]-[B]-[A']-3', wherein [A] is the sense strand containing a sequence corresponding to a target sequence of SEQ ID NO: 17, [B] is the intervening single strand composed of 3 to 23 nucleotides, and [A'] is the anti-sense strand containing a sequence complementary to [A];

[12] The method of [1], wherein the double-stranded molecule is an RNA;

[13] The method of [1], wherein the double-stranded molecule contains both DNA and RNA;

[14] The method of [13], wherein the double-stranded molecule is a hybrid of a DNA polynucleotide and an RNA polynucleotide;

[15] The method of [14] wherein the sense and anti-sense strand polynucleotides are composed of DNA and RNA, respectively;

[16] The method of [13], wherein the double-stranded molecule is a chimera of DNA and RNA;

[17] The method of [16], wherein a region flanking to the 3'-end of the anti-sense strand, or both of a region flanking to the 5'-end of sense strand and a region flanking to the 3'-end of anti-sense strand are composed of RNA;

[18] The method of [17], wherein the flanking region is composed of 9 to 13 nucleotides;

[19] The method of [1], wherein the double-stranded molecule contains 3' overhangs;

[20] The method of [1], wherein the double-stranded molecule is contained in a composition which includes, in addition to the molecule, a transfection-enhancing agent and pharmaceutically acceptable carrier.

[21] The method of [1], wherein the double-stranded molecule is encoded by a vector;

[22] The method of [21], wherein the double-stranded molecule encoded by the vector acts at mRNA which matches a target sequence of SEQ ID NO: 17 (at the position of 803-821 nt of SEQ ID NO: 1).

[23] The method of [22], wherein the sense strand of the double-stranded molecule encoded by the vector contains the sequence corresponding to a target sequence selected from among SEQ ID NO: 17.

[24] The method of [21], wherein the cancer to be treated is bladder cancer, gastric cancer, colorectal cancer, breast cancer, esophageal cancer, lung cancer, lymphoma, pancreatic cancer and testicular cancer;

[25] The method of [23], wherein the double-stranded molecule encoded by the vector has a length of less than about 100 nucleotides;

[26] The method of [25], wherein the double-stranded molecule encoded by the vector has a length of less than about 75 nucleotides;

[27] The method of [26], wherein the double-stranded molecule encoded by the vector has a length of less than about 50 nucleotides;

[28] The method of [27], wherein the double-stranded molecule encoded by the vector has a length of less than about 25 nucleotides;

[29] The method of [28], wherein the double-stranded molecule encoded by the vector has a length of between about 19 and about 25 nucleotides in length;

[30] The method of [21], wherein the double-stranded molecule encoded by the vector is composed of a single polynucleotide containing both the sense strand and the antisense strand linked by an intervening single-strand;

[31] The method of [30], wherein the double-stranded molecule encoded by the vector has the general formula 5'-[A]-[B]-[A']-3', wherein [A] is the sense strand containing a sequence corresponding to a target sequence of SEQ ID NO: 17, [B] is a intervening single-strand is composed of 3 to 23 nucleotides, and [A'] is the anti-sense strand containing a sequence complementary to [A]; and

[32] The method of [21], wherein the double-stranded molecule encoded by the vector is contained in a composition which includes, in addition to the molecule, a transfection-enhancing agent and pharmaceutically acceptable carrier.

The method of the present invention will be described in more detail below.

The growth of cells expressing PRMT1 gene may be inhibited by contacting the cells with a double-stranded molecule against PRMT1 gene, a vector expressing the molecule or a composition containing the same. The cell may be further contacted with a transfection agent. Suitable transfection agents are known in the art. The phrase "inhibition of cell growth" indicates that the cell proliferates at a lower rate or has decreased viability as compared to a cell not exposed to the molecule. Cell growth may be measured by methods known in the art, e.g., using the MTT cell proliferation assay.

The growth of any kind of cell may be suppressed according to the present method so long as the cell expresses or over-expresses the target gene of the double-stranded molecule of the present invention. Exemplary cells include bladder cancer, gastric cancer, colorectal cancer, breast cancer, esophageal cancer, lung cancer, lymphoma, pancreatic cancer and testicular cancer.

Thus, patients suffering from or at risk of developing disease related to PRMT1 may be treated by administering the present double-stranded molecule, at least one vector expressing the molecule or composition containing the molecule. For example, cancer patients may be treated according to the present methods. The type of cancer may be identified by standard methods according to the particular type of tumor to be diagnosed. More preferably, patients treated by the methods of the present invention are selected by detecting the expression of PRMT1 in a biopsy from the patient by RT-PCR or immunoassay. Preferably, before the treatment of the present invention, the biopsy specimen from the subject is confirmed for PRMT1 gene over-expression by methods known in the art, for example, immunohistochemical analysis or RT-PCR.

For inhibiting cell growth, a double-stranded molecule of present invention may be directly introduced into the cells in a form to achieve binding of the molecule with corresponding mRNA transcripts. Alternatively, as described above, a DNA encoding the double-stranded molecule may be introduced into cells as a vector. For introducing the double-stranded molecules and vectors into the cells, transfection-enhancing agent, such as FuGENE (Roche diagnostics), Lipofectamine 2000 (Invitrogen), Oligofectamine (Invitrogen), and Nucleofector (Wako pure Chemical), may be employed.

A treatment is deemed "efficacious" if it leads to clinical benefit such as, reduction in expression of PRMT1 gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

It is understood that the double-stranded molecule of the invention degrades the t PRMT1 mRNA in substoichiometric amounts. Without wishing to be bound by any theory, it is believed that the double-stranded molecule of the invention causes degradation of the target mRNA in a catalytic manner. Thus, compared to standard cancer therapies, significantly less a double-stranded molecule needs to be delivered at or near the site of cancer to exert therapeutic effect.

One skilled in the art can readily determine an effective amount of the double-stranded molecule of the invention to be administered to a given subject, by taking into account factors such as body weight, age, sex, type of disease, symptoms and other conditions of the subject; the route of administration; and whether the administration is regional or systemic. Generally, an effective amount of the double-stranded molecule of the invention is an intercellular concentration at or near the cancer site of from about 1 nanomolar (nM) to about 100 nM, preferably from about 2 nM to about 50 nM, more preferably from about 2.5 nM to about 10 nM. It is contemplated that greater or smaller amounts of the double-stranded molecule can be administered. The precise dosage required for a particular circumstance may be readily and routinely determined by one of skill in the art.

The present methods can be used to inhibit the growth or metastasis of cancer expressing at least one PRMT1; for example bladder cancer, gastric cancer, colorectal cancer, breast cancer, esophageal cancer, lung cancer, lymphoma, pancreatic cancer and testicular cancer. In particular, a double-stranded molecule containing a target sequence of PRMT1 (i.e., SEQ ID NO: 17) is particularly preferred for the treatment of cancer.

For treating cancer, the double-stranded molecule of the present invention can also be administered to a subject in combination with a pharmaceutical agent different from the double-stranded molecule. Alternatively, the double-stranded molecule of the present invention can be administered to a subject in combination with another therapeutic method designed to treat cancer. For example, the double-stranded molecule of the present invention can be administered in combination with therapeutic methods currently employed for treating cancer or preventing cancer metastasis (e.g., radiation therapy, surgery and treatment using chemotherapeutic agents, such as cisplatin, carboplatin, cyclophosphamide, 5-fluorouracil, adriamycin, daunorubicin or tamoxifen).

In the present methods, the double-stranded molecule can be administered to the subject either as a naked double-stranded molecule, in conjunction with a delivery reagent, or as a recombinant plasmid or viral vector which expresses the double-stranded molecule.

Suitable delivery reagents for administration in conjunction with the present a double-stranded molecule include the Mirus Transit TKO lipophilic reagent; lipofectin; lipofectamine; cellfectin; or polycations (e.g., polylysine), or liposomes. A preferred delivery reagent is a liposome.

Liposomes can aid in the delivery of the double-stranded molecule to a particular tissue, such as lung tumor tissue, and can also increase the blood half-life of the double-stranded molecule. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al., Ann Rev Biophys Bioeng 1980, 9: 467; and U.S. Pat. Nos. 4,235,871; 4,501,728; 4,837,028; and 5,019,369, the entire disclosures of which are herein incorporated by reference.

Preferably, the liposomes encapsulating the present double-stranded molecule comprises a ligand molecule that can deliver the liposome to the cancer site. Ligands which bind to receptors prevalent in tumor or vascular endothelial cells, such as monoclonal antibodies that bind to tumor antigens or endothelial cell surface antigens, are preferred.

Particularly preferably, the liposomes encapsulating the present double-stranded molecule are modified so as to avoid clearance by the mononuclear macrophage and reticuloendothelial systems, for example, by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example, solid tumors, will efficiently accumulate these liposomes; see Gabizon et al., Proc Natl Acad Sci USA 1988, 18: 6949-53. In addition, the reduced uptake by the RES lowers the toxicity of stealth liposomes by preventing significant accumulation in liver and spleen. Thus, liposomes of the invention that are modified with opsonization-inhibition moieties can deliver the present double-stranded molecule to tumor cells.

Opsonization inhibiting moieties suitable for modifying liposomes are preferably water-soluble polymers with a molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM.sub.1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes".

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH.sub.3 and a solvent mixture such as tetrahydrofuran and water in a 30:12 ratio at 60 degrees C.

Vectors expressing a double-stranded molecule of the invention are discussed above. Such vectors expressing at least one double-stranded molecule of the invention can also be administered directly or in conjunction with a suitable delivery reagent, including the Mirus Transit LT1 lipophilic reagent; lipofectin; lipofectamine; cellfectin; polycations (e.g., polylysine) or liposomes. Methods for delivering recombinant viral vectors, which express a double-stranded molecule of the invention, to an area of cancer in a patient are within the skill of the art.

The double-stranded molecule of the present invention can be administered to the subject by any means suitable for delivering the double-stranded molecule into cancer sites. For example, the double-stranded molecule can be administered by gene gun, electroporation, or by other suitable parenteral or enteral administration routes.

Suitable enteral administration routes include oral, rectal, or intranasal delivery.

Suitable parenteral administration routes include intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection); subcutaneous injection or deposition including subcutaneous infusion (such as by osmotic pumps); direct application to the area at or near the site of cancer, for example by a catheter or other placement device (e.g., a suppository or an implant comprising a porous, non-porous, or gelatinous material); and inhalation. It is preferred that injections or infusions of the double-stranded molecule or vector be given at or near the site of cancer.

The double-stranded molecule of the present invention can be administered in a single dose or in multiple doses. Where the administration of the double-stranded molecule of the invention is by infusion, the infusion can be a single sustained dose or can be delivered by multiple infusions. Injection of the agent directly into the tissue is at or near the site of cancer preferred. Multiple injections of the agent into the tissue at or near the site of cancer are particularly preferred.

One skilled in the art can also readily determine an appropriate dosage regimen for administering the double-stranded molecule of the invention to a given subject. For example, the double-stranded molecule can be administered to the subject once, for example, as a single injection or deposition at or near the cancer site. Alternatively, the double-stranded molecule can be administered once or twice daily to a subject for a period of from about three to about twenty-eight days, more preferably from about seven to about ten days. In a preferred dosage regimen, the double-stranded molecule is injected at or near the site of cancer once a day for seven days. Where a dosage regimen comprises multiple administrations, it is understood that the effective amount of a double-stranded molecule administered to the subject can comprise the total amount of a double-stranded molecule administered over the entire dosage regimen.

Compositions Containing a Double-Stranded Molecule of the Present Invention:

In addition to the above, the present invention also provides pharmaceutical composition that include the present double-stranded molecule or the vector coding for the molecules. Specifically, the present invention provides the following compositions [1] to [32]:

[1] A composition for inhibiting a growth of cancer cell and treating a cancer, wherein the cancer cell and the cancer expresses a PRMT1 gene, including isolated double-stranded molecule inhibiting the expression of PRMT1 and the cell proliferation, which molecule is composed of a sense strand and an anti-sense strand complementary thereto, hybridized to each other to form the double-stranded molecule.

[2] The composition of [1], wherein the double-stranded molecule acts at mRNA which matches a target sequence of SEQ ID NO: 17 (at the position of 803-821 nt of SEQ ID NO: 1).

[3] The composition of [2], wherein the double-stranded molecule, wherein the sense strand contains a sequence corresponding to a target sequence of SEQ ID NO: 17.

[4] The composition of [1], wherein the cancer to be treated is bladder cancer, gastric cancer, colorectal cancer, breast cancer, esophageal cancer, lung cancer, lymphoma, pancreatic cancer and testicular cancer;

[5] The composition of [3], wherein the double-stranded molecule has a length of less than about 100 nucleotides;

[6] The composition of [5], wherein the double-stranded molecule has a length of less than about 75 nucleotides;

[7] The composition of [6], wherein the double-stranded molecule has a length of less than about 50 nucleotides;

[8] The composition of [7], wherein the double-stranded molecule has a length of less than about 25 nucleotides;

[9] The composition of [8], wherein the double-stranded molecule has a length of between about 19 and about 25 nucleotides;

[10] The composition of [1], wherein the double-stranded molecule is composed of a single polynucleotide containing the sense strand and the anti-sense strand linked by an intervening single-strand;

[11] The composition of [10], wherein the double-stranded molecule has the general formula 5'-[A]-[B]-[A']-3', wherein [A] is the sense strand sequence contains a sequence corresponding to a target sequence of SEQ ID NO: 17, [B] is the intervening single-strand consisting of 3 to 23 nucleotides, and [A'] is the anti-sense strand contains a sequence complementary to [A];

[12] The composition of [1], wherein the double-stranded molecule is an RNA;

[13] The composition of [1], wherein the double-stranded molecule is DNA and/or RNA;

[14] The composition of [13], wherein the double-stranded molecule is a hybrid of a DNA polynucleotide and an RNA polynucleotide;

[15] The composition of [14], wherein the sense and anti-sense strand polynucleotides are composed of DNA and RNA, respectively;

[16] The composition of [13], wherein the double-stranded molecule is a chimera of DNA and RNA;

[17] The composition of [14], wherein a region flanking to the 3'-end of the anti-sense strand, or both of a region flanking to the 5'-end of sense strand and a region flanking to the 3'-end of anti-sense strand are composed of RNA;

[18] The composition of [17], wherein the flanking region is composed of 9 to 13 nucleotides;

[19] The composition of [1], wherein the double-stranded molecule contains 3' overhangs;

[20] The composition of [1], wherein the composition includes a transfection-enhancing agent and pharmaceutically acceptable carrier.

[21] The composition of [1], wherein the double-stranded molecule is encoded by a vector and contained in the composition;

[22] The composition of [21], wherein the double-stranded molecule encoded by the vector acts at mRNA which matches a target sequence of SEQ ID NO: 17 (at the position of 803-821 nt of SEQ ID NO: 1).

[23] The composition of [22], wherein the sense strand of the double-stranded molecule encoded by the vector contains the sequence corresponding to a target sequence of SEQ ID NO: 17.

[24] The composition of [21], wherein the cancer to be treated is bladder cancer, gastric cancer, colorectal cancer, breast cancer, esophageal cancer, lung cancer, lymphoma, pancreatic cancer and testicular cancer;

[25] The composition of [23], wherein the double-stranded molecule encoded by the vector has a length of less than about 100 nucleotides;

[26] The composition of [25], wherein the double-stranded molecule encoded by the vector has a length of less than about 75 nucleotides;

[27] The composition of [26], wherein the double-stranded molecule encoded by the vector has a length of less than about 50 nucleotides;

[28] The composition of [27], wherein the double-stranded molecule encoded by the vector has a length of less than about 25 nucleotides;

[29] The composition of [28], wherein the double-stranded molecule encoded by the vector has a length of between about 19 and about 25 nucleotides in length;

[30] The composition of [21], wherein the double-stranded molecule encoded by the vector is composed of a single polynucleotide containing both the sense strand and the anti-sense strand linked by an intervening single-strand;

[31] The composition of [30], wherein the double-stranded molecule has the general formula 5'-[A]-[B]-[A']-3', wherein [A] is the sense strand containing a sequence corresponding to a target sequence of SEQ ID NO: 17, [B] is a intervening single-strand composed of 3 to 23 nucleotides, and [A'] is the anti-sense strand containing a sequence complementary to [A]; and

[32] The composition of [21], wherein the composition includes a transfection-enhancing agent and pharmaceutically acceptable carrier.

Suitable compositions of the present invention are described in additional detail below.

The double-stranded molecule of the invention is preferably formulated as pharmaceutical compositions prior to administering to a subject, according to techniques known in the art. Pharmaceutical composition of the present invention is characterized as being at least sterile and pyrogen-free. As used herein, "pharmaceutical composition" includes formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

The present pharmaceutical composition contains the double-stranded molecule or vector encoding that of the present invention (e.g., 0.1 to 90% by weight), or a physiologically acceptable salt of the molecule, mixed with a physiologically acceptable carrier medium. Preferred physiologically acceptable carrier media are water, buffered water, normal saline, 0.4% saline, 0.3% glycine, hyaluronic acid and the like.

Moreover, the present double-stranded molecule may be contained as liposomes in the present composition. See under the item of "Methods of treating cancer using the double-stranded molecule" for details of liposomes.

Pharmaceutical compositions of the invention can also include conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can include any of the carriers and excipients listed above and 10-95%, preferably 25-75%, of one or more double-stranded molecule of the invention. A pharmaceutical composition for aerosol (inhalational) administration can comprise 0.01-20% by weight, preferably 1-10% by weight, of one or more double-stranded molecule of the invention encapsulated in a liposome as described above, and propellant. A carrier can also be included as desired; e.g., lecithin for intranasal delivery.

In addition to the above, the present composition may contain other pharmaceutical active ingredients so long as they do not inhibit the in vivo function of the present double-stranded molecules. For example, the composition may contain chemotherapeutic agents conventionally used for treating cancers.

In another embodiment, the present invention also provides the use of the double-stranded nucleic acid molecule of the present invention in manufacturing a pharmaceutical composition for treating a cancer characterized by the expression of PRMT1. For example, the present invention relates to a use of double-stranded nucleic acid molecule inhibiting the expression of PRMT1 gene in a cell, which molecule includes a sense strand and an anti-sense strand complementary thereto, hybridized to each other to form the double-stranded nucleic acid molecule and target to a sequence of SEQ ID NO: 17, for manufacturing a pharmaceutical composition for treating cancer expressing PRMT1.

Alternatively, the present invention further provides a method or process for manufacturing a pharmaceutical composition for treating a cancer characterized by the expression of PRMT1, wherein the method or process includes a step for formulating a pharmaceutically or physiologically acceptable carrier with a double-stranded nucleic acid molecule inhibiting the expression of PRMT1 in a cell, which over-expresses the gene, which molecule includes a sense strand and an anti-sense strand complementary thereto, hybridized to each other to form the double-stranded nucleic acid molecule and target to a sequence of SEQ ID NO: 17 as active ingredients.

In another embodiment, the present invention also provides a method or process for manufacturing a pharmaceutical composition for treating a cancer characterized by the expression of PRMT1, wherein the method or process includes a step for admixing an active ingredient with a pharmaceutically or physiologically acceptable carrier, wherein the active ingredient is a double-stranded nucleic acid molecule inhibiting the expression of PRMT1 in a cell, which over-expresses the gene, which molecule includes a sense strand and an anti-sense strand complementary thereto, hybridized to each other to form the double-stranded nucleic acid molecule and targets to a sequence of SEQ ID NO: 17.

Hereinafter, the present invention is described in more detail with reference to the Examples. However, the following materials, methods and examples only illustrate aspects of the invention and in no way are intended to limit the scope of the present invention. As such, methods and materials similar or equivalent to those described herein can be used in the practice or testing of the present invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The invention will be further described in the following examples, which do not limit the scope of the invention described in the claims.

Example 1

General Methods

Tissue samples and RNA preparation.

126 surgical specimens of primary urothelial cell carcinoma were collected, either at cystectomy or trans-urethral resection, and snap frozen in liquid nitrogen. Thirty-four specimens of normal bladder urothelium were collected from areas of macroscopically normal urothelium in patients with no evidence of urothelial malignancy. A total of 30 sections of 30 micro-m (micro meter) were homogenized for RNA extraction and two 7 micro-m 'sandwich' sections adjacent to the tissue used for RNA extraction were sectioned, stained and assessed for cellularity and tumor grade by an independent consultant urohistopathologist. Additionally, the sections were graded according to the degree of inflammatory cell infiltration (low, moderate and significant). Samples showing significant inflammatory cell infiltration were excluded (Wallard M J, et al., Br J Cancer 2006; 94:569-577).

Total RNA was extracted using TRI Reagent™ (Sigma, Dorset, UK), following the manufacturers protocol. RNEasy Minikits™ (Qiagen, Crawley, UK), including a DNase step, were used to optimize RNA purity. Agilent 2100™ total RNA bioanalysis was performed. One microliter of resuspended RNA from each sample was applied to an RNA 6000 Nano-LabChip™, and processed according to the manufacturer's instructions. All chips and reagents were sourced from Agilent Technologies™ (West Lothian, UK).

Reverse Transcription.

Total RNA concentrations were determined using the Nanodrop™ ND 1000 spectrophotometer (Nyxor Biotech, Paris, France). One microgram of total RNA was reverse transcribed with 2 micro-g (micro gram) random hexamers (Amersham) and Superscript III reverse transcriptase (Invitrogen, Paisley, UK) in 20 micro-l (micro litter) reactions according to the manufacturer's instructions. cDNA was then diluted 1:100 with PCR grade water and stored at −20 degrees C.

Quantitative RT-PCR.

For quantitative RT-PCR reactions, specific primers for all human GAPDH (housekeeping gene), SDH (housekeeping gene), OMD and PRELP were designed (Table 1). For 18S amplification, TaqMan Ribosomal RNA Control Reagents were purchased from Applied Biosystems, Warrington, UK. PCR reactions were performed using the ABI prism 7700 Sequence Detection System (Applied Biosystems, Warrington, UK) following the manufactures protocol. Reactions for 18S analyses were performed in 10 micro-l PCR volumes containing the equivalent of 1 ng of reverse transcribed RNA, 50% SYBR GREEN universal PCR Master Mix without UNG (Applied Biosystems, Warrington, UK), 200 nM each of the forward and reverse primers and 100 nM of probe.

Amplification conditions were 2 min at 50 degrees C., 10 min at 95 degrees C. and then 40 cycles each consisting of 15 s at 95 degrees C. and 1 min at 60 degrees C. Reaction conditions for target gene amplification were as described above and the equivalent of 5 ng of reverse transcribed RNA was used in each reaction.

TABLE 1

Primer sequences for quantitative RT-PCR

| Gene name | Primer sequence | SEQ ID NO: |
|---|---|---|
| GAPDH-f | 5' GCAAATTCCATGGCACCGTC 3' | 3 |
| GAPDH-r | 5' TCGCCCCACTTGATTTTGG 3' | 4 |
| SDH-f | 5' TGGGAACAAGAGGGCATCTG 3' | 5 |
| SDH-r | 5' CCACCACTGCATCAAATTCATG 3' | 6 |
| PRMT1-f1 | 5' GGGCTACTGCCTCTTCTACGAGTC 3' | 7 |
| PRMT1-r1 | 5' GTCTTTGTACTGCCGGTCCTCGATG 3' | 8 |
| PRMT1-f2 | 5' GGTGGACATCATCATCAGCGAGTGG 3' | 9 |
| PRMT1-r2 | 5' TCACATACAGCGTGGCCCGGTCTGG 3' | 10 |

To determine relative RNA levels within the samples, standard curves for the PCR reactions were prepared from a series of two-fold dilutions of cDNA covering the range 2-0.625 ng of RNA for the 18S reaction and 20-0.5 ng of RNA for all target genes. The ABI prism 7700 measured changes in fluorescence levels throughout the 40 cycle PCR reaction and generated a cycle threshold (Ct) value for each sample correlating to the point at which amplification entered the exponential phase. This value was used as an indicator of the amount of starting template; hence a lower Ct values indicated a higher amount of initial intact cDNA.

Laser Capture Microdissection.

Tissue for laser capture microdissection was collected prospectively following the procedure outlined above. Five sequential sections of 7 micro-m thickness were cut from each tissue and stained using Histogene™ staining solution (Arcturus, Calif., USA) following the manufacturer's protocol. Slides were then immediately transferred for microdissection using a Pix Cell II laser capture microscope (Arcturus, Calif., USA). This technique employs a low-power infrared laser to melt a thermoplastic film over the cells of interest, to which the cells become attached.

Approximately 10000 cells were microdissected from both stromal and epithelial/tumor compartments in each tissue. RNA was extracted using an RNEasy Micro Kit (Qiagen, Crawley, UK). Areas of cancer or stroma containing significant inflammatory areas of tumor or stroma containing significant inflammatory cell infiltration were avoided to prevent contamination.

Total RNA was reverse transcribed and qRT-PCR performed as above. Given the low yield of RNA from such small samples, Nanodrop™ quantification was not performed, but correction for the endogenous 18S CT value was used as an accurate measure of the amount of intact starting RNA. Transcript analysis was performed for the PRMT1 genes To validate the accuracy of microdissection, primers and probes for Vimentin and Uroplakin were sourced and qRT-PCR performed according to the manufacturer's instructions (Assays on demand, Applied Biosystems, Warrington, UK). Vimentin is primarily expressed in messenchymally derived cells, and was used as a stromal marker. Uroplakin is a marker of urothelial differentiation and is preserved in up to 90% of epithelially derived tumors (Olsburgh J, et al., J Pathol 2003; 199:41-49).

cDNA Microarray.

A genome-wide cDNA microarray was fabricated with 36864 cDNAs selected from the UniGene database of the National Center for Biotechnology Information (NCBI). This microarray system was constructed essentially as described previously (Ono K, et al., Cancer Res 2000; 60:5007-5011). Briefly, the cDNAs were amplified by RT-PCR using poly (A)+ RNAs isolated from various human organs as templates; the lengths of the amplicons ranged from 200 to 1100 bp, without any repetitive or poly (A) sequences.

Transfection of siRNAs. siRNA oligonucleotide duplexes were purchased from SIGMA Genosys for targeting the human PRMT1 transcript or the EGFP and FFLuc transcripts as control siRNAs. The siRNA sequences are described in Table 2. siRNA duplexes (100 nM final concentration) were transfected in bladder and lung cancer cell lines with lipofectamine-2000 (Invitrogen) for 48 hr, and checked the cell viability using cell counting kit 8 (DOJINDO).

TABLE 2 siRNA Sequences

| Target gene name | Sequence | SEQ ID NO: |
|---|---|---|
| EGFP-target | 5' GCAGCACGACTTCTTCAAG 3' | 11 |
| EGFP-forward | 5' GCAGCACGACUUCUUCAAGTT 3' | 12 |
| EGFP-reverse | 5' CUUGAAGAAGUCGUGCUGCTT 3' | 13 |
| FFLuc-target | 5' GTGCGCTGCTGGTGCCAAC 3' | 14 |
| FFLuc-forward | 5' GUGCGCUGCUGGUGCCAACTT 3' | 15 |
| FFLuc-reverse | 5' GUUGGCACCAGCAGCGCACTT 3' | 16 |
| PRMT1#2-target | 5' GAGTTCACACGCTGCCACA 3' | 17 |
| PRMT1#2-forward | 5' GAGUUCACACGCUGCCACATT 3' | 18 |
| PRMT1#2-reverse | 5' UGUGGCAGCGUGUGAACUCTT 3' | 19 |

Example 2

Expression Levels of PRMT1 in Clinical Cancer Tissues and Subcellular Localization of PRMT1 Proteins The initial results comparing expression levels of several PRMT1 family genes using a small number of clinical bladder samples showed the significant difference of PRMT1 expression between normal and tumor tissues (data not shown). Therefore, further analysis of a large number of clinical samples was carried out to quantitatively measure transcript levels of PRMT1. 121 bladder cancer and 24 normal control samples were analyzed (FIGS. 1A and B). The expression levels of PRMT1 were found to be significantly higher in tumors compared with normal tissues (P<0.0001). The expression profile of PRMT1 was also checked in many types of cancer using a number of clinical samples from Japanese subjects by cDNA microarray (Table 3). The expression levels of PRMT1 are significantly up-regulated in diffuse-type gastric cancer, colorectal cancer, breast cancer, esophageal cancer, small cell lung cancer, lymphoma, non-small cell lung cancer, pancreatic cancer and testicular cancer compared with corresponding nonneoplastic tissues.

TABLE 3

The gene expression profile of PRMT1 in cancer tissues

| Tissue type | Case (n) | Up-regulated Ratio (Tumor/Normal) | | | |
|---|---|---|---|---|---|
| | | Above 2 | Above 3 | Above 5 | Above 10 |
| Diffuse-type gastric cancer | 17 | 13 (76.4%) | 7 (41.2%) | 3 (17.6%) | 0 (0%) |
| Colorectal cancer | 39 | 15 (38.5%) | 12 (30.8%) | 10 (25.6%) | 4 (10.3%) |
| Breast cancer | 71 | 15 (21.1%) | 12 (16.9%) | 9 (12.7%) | 7 (10.0%) |
| Esophageal cancer | 61 | 13 (21.3%) | 5 (8.2%) | 2 (3.3%) | 2 (3.3%) |
| Small cell lung cancer | 15 | 11 (73.3%) | 6 (40%) | 0 (0%) | 0 (0%) |
| Lymphoma | 20 | 6 (30.0%) | 1 (5.0%) | 1 (5.0%) | 1 (5.0%) |
| Non-small cell lung cancer | 12 | 9 (75.0%) | 5 (41.7%) | 3 (25.0%) | 3 (25.0%) |
| Pancreatic cancer | 16 | 6 (37.5%) | 2 (12.5%) | 2 (12.5%) | 0 (0%) |
| Testicular cancer | 10 | 7 (70.0%) | 7 (70.0%) | 7 (70.0%) | 1 (14.3%) |

The expression levels of these genes were analyzed by cDNA microarray.

The signal intensity of PRMT1 were made with a comparison between tumour tissues and corresponding non-neoplatic tissues derived from the same patient.

Moreover, plasmids expressing V5-tagged PRMT1 (pcDNA5/FRT/V5-His-PRMT1) were prepared and transfected into Flp-In T-REx 293 cells, which contains a Flp recombination target (FRT) site in its genome. Immunoblot analysis using extracts from Flp-In T-REx 293 showed a 40-kDa band corresponding to the tagged PRMT1 protein (FIG. 1C). Immunocytochemical staining of the T-REx 293-PRMT1 cells revealed that the tagged PRMT1 proteins were present in both their cytoplasm and nucleus (FIG. 1D).

Example 3

Expression Levels of PRMT1 in Human Normal Tissues

The gene-expression profiles of PRMT1 were analyzed in 25 adult and 4 fetal human tissues on the cDNA microarray, using a mixture of poly(A)+ RNAs from all 29 tissues as a control to calculate the relative expression ratio (Cy5/Cy3) of each of the 36864 genes on the array. The intensity of each hybridization signal was calculated photo-metrically by the Array Vision computer program and background intensity was subtracted. Normalization of each Cy3- and Cy5-fluorescence intensity was performed using averaged signals from the 52 housekeeping genes. The detailed analytical result indicated that expression levels of PRMT1 in all checked normal tissues were significantly low compared with those of GAPDH (FIG. 2). As average signal intensity of PRMT1 in all normal tissues was around 10000, this value was relatively low among the 36864 genes. Consequently, PRMT1 was regarded as a good candidate of cancer therapy.

Example 4

Effect of PRMT1 Suppression on the Viability of Cancer Cells

To test whether elevated expression of PRMT1 may play a crucial role in the proliferation of cancer cells, siRNA oligonucleotide duplexes, which specifically suppress the expression of PRMT1 (siPRMT1#2), together with two controls (siEGFP and siFFLuc), were prepared and transfected into several lung and bladder cancer cell lines that expressed PRMT1 abundantly. As shown in FIG. 3A, siPRMT1#2 significantly suppressed the expression of PRMT1 compared with siEGFP as a control. Subsequently, to test whether suppression of PRMT1 may result in growth retardation and/or cell death, cancer cells were transfected with siRNA oligonucleotide duplexes and the growth transfected cells were examined by cell counting kit system (FIG. 3B). Importantly, transfection of siPRMT1#2 into four lung cancer cell lines (A549, RERFLC-A1, LC319 and SBC5) and two bladder cancer cell lines (SW780 and SCaBER) reduced their ability when compared with cells transfected with siEGFP and siFFLuc. In addition, the data of cell cycle analysis using SW780 bladder cancer cells showed that cells in S phase significantly decreased after treatment with siPRMT1#2, and cells in Go and G1 phase coincidentally increased (Table 4). These data suggest that PRMT1 may play an essential role in the growth or survival of lung and bladder cancer cells.

TABLE 4

Cell cycle analysis of SW780 cells after treatment with siRNAs

| siRNA name | G0/G1 | S | G2/M |
|---|---|---|---|
| siEGFP | 47.04 ± 4.18*[1] | 32.45 ± 2.70*[3] | 18.33 ± 3.52 |
| siFFLuc | 56.58 ± 2.00*[2] | 27.07 ± 2.26*[4] | 13.31 ± 1.28 |
| siPRMT1#2 | 77.15 ± 6.21*[1,*2] | 11.83 ± 2.61*[3,*4] | 12.79 ± 3.53 |

*[1] $p = 0.0173$,
*[2] $p = 0.0110$,
*[3] $p = 0.0107$,
*[4] $p = 0.0022$;
The p value was calculated by Student's t-test.

Industrial Applicability

The present inventors have shown that the cell growth is suppressed by a double-stranded nucleic acid molecule that specifically targets the PRMT1 gene. Thus, the double-stranded nucleic acid molecule is useful for the development of anti-cancer pharmaceuticals. For example, agents that block the expression of PRMT1 protein or prevent its activity may find therapeutic utility as anti-cancer agents, particularly anti-cancer agents for the treatment of bladder cancer, gastric cancer, colorectal cancer, breast cancer, esophageal cancer, lung cancer, lymphoma, pancreatic cancer, or testicular cancer.

While the invention has been described in detail and with reference to specific embodiments thereof, it will be apparent to one skilled in the art that various changes and modifications can be made therein without departing from the spirit and scope of the invention. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention claimed is:

1. A method of screening for a candidate compound for treating or preventing cancer or inhibiting cancer cell growth, said method comprising the steps of:
   (a) contacting a test compound with a polypeptide encoded by PRMT1 gene;
   (b) detecting the binding activity between the polypeptide and the test compound or detecting the biological activity of the polypeptide of step (a);
   (c) selecting a compound that binds to the polypeptide or selecting the test compound that suppresses the biological activity of the polypeptide in comparison with the biological activity detected in the absence of the test compound and
   (d) contacting the test compound identified in step (c) with cancer cells that over-express PRMT1 selected from the group consisting of bladder cancer, gastric cancer, colorectal cancer, esophageal cancer, lung cancer, lymphoma, pancreatic cancer, and testicular cancer;
   (e) measuring cell-proliferation activity; and
   (f) selecting the test compound that reduces the cell-proliferation activity in comparison with the cell proliferation activity in the absence of test compound.

2. The method of claim 1, wherein the biological activity is methyltransferase activity.

* * * * *

UNITED STATES PATENT AND TRADEMARK OFFICE
CERTIFICATE OF CORRECTION

PATENT NO. : 8,512,944 B2
APPLICATION NO. : 13/060672
DATED : August 20, 2013
INVENTOR(S) : Nakamura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 72 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 19

<210> SEQ ID NO 1
<211> LENGTH: 1131
<212> TYPE: DNA
<213> ORGANISM: Homo sapiens

<400> SEQUENCE: 1

| | |
|---|---|
| ggccgcgaac tgcatcatgg aggtgtcctg tggccaggcg aaaagcagtg agaagcccaa | 60 |
| cgctgaggac atgacatcca aagattacta ctttgactcc tacgcacact ttggcatcca | 120 |
| cgaggagatg ctgaaggacg aggtgcgcac cctcacttac cgcaactcca tgtttcataa | 180 |
| ccggcacctc ttcaaggaca aggtggtgct ggacgtcggc tcgggcaccg gcatcctctg | 240 |
| catgtttgct gccaaggccg ggcccgcaa ggtcatcggg atcgagtgtt ccagtatctc | 300 |
| tgattatgcg gtgaagatcg tcaaagccaa caagttagac cacgtggtga ccatcatcaa | 360 |
| ggggaaggtg gaggaggtgg agctcccagt ggagaaggtg gacatcatca tcagcgagtg | 420 |
| gatgggctac tgcctcttct acgagtccat gctcaacacc gtgctctatg cccgggacaa | 480 |
| gtggctggcg cccgatggcc tcatcttccc agaccgggcc acgctgtatg tgacggccat | 540 |
| cgaggaccgg cagtacaaag actacaagat ccactggtgg agaacgtgt atggcttcga | 600 |
| catgtcttgc atcaaagatg tggccattaa ggagcccta gtggatgtcg tggaccccaa | 660 |
| acagctggtc accaacgcct gcctcataaa ggaggtggac atctataccg tcaaggtgga | 720 |
| agacctgacc ttcacctccc cgttctgcct gcaagtgaag cggaatgact acgtgcacgc | 780 |
| cctggtggcc tacttcaaca tcgagttcac acgctgccac aagaggaccg gcttctccac | 840 |
| cagccccgag tccccgtaca cgcactggaa gcagacggtg ttctacatgg aggactacct | 900 |
| gaccgtgaag acgggcgagg agatcttcgg caccatcggc atgcggccca acgccaagaa | 960 |
| caaccgggac ctggacttca ccatcgacct ggacttcaag ggccagctgt gcgagctgtc | 1020 |
| ctgctccacc gactaccgga tgcgctgagg cccggctctc ccgccctgca cgagcccagg | 1080 |
| ggctgagcgt tcctaggcgg tttcgggct ccccttcct ctccctccct c | 1131 |

<210> SEQ ID NO 2
<211> LENGTH: 343
<212> TYPE: PRT
<213> ORGANISM: Homo sapiens

<400> SEQUENCE: 2

Met Glu Val Ser Cys Gly Gln Ala Glu Ser Ser Glu Lys Pro Asn Ala
1               5                   10                  15

Glu Asp Met Thr Ser Lys Asp Tyr Tyr Phe Asp Ser Tyr Ala His Phe
            20                  25                  30

Gly Ile His Glu Glu Met Leu Lys Asp Glu Val Arg Thr Leu Thr Tyr
        35                  40                  45

Arg Asn Ser Met Phe His Asn Arg His Leu Phe Lys Asp Lys Val Val
    50                  55                  60

Leu Asp Val Gly Ser Gly Thr Gly Ile Leu Cys Met Phe Ala Ala Lys
65                  70                  75                  80

Ala Gly Ala Arg Lys Val Ile Gly Ile Glu Cys Ser Ser Ile Ser Asp
                85                  90                  95

Tyr Ala Val Lys Ile Val Lys Ala Asn Lys Leu Asp His Val Val Thr
            100                 105                 110

Ile Ile Lys Gly Lys Val Glu Glu Val Glu Leu Pro Val Glu Lys Val

```
                    115                 120                 125
Asp Ile Ile Ser Glu Trp Met Gly Tyr Cys Leu Phe Tyr Glu Ser
130                 135                 140

Met Leu Asn Thr Val Leu Tyr Ala Arg Asp Lys Trp Leu Ala Pro Asp
145                 150                 155                 160

Gly Leu Ile Phe Pro Asp Arg Ala Thr Leu Tyr Val Thr Ala Ile Glu
                165                 170                 175

Asp Arg Gln Tyr Lys Asp Tyr Lys Ile His Trp Trp Glu Asn Val Tyr
            180                 185                 190

Gly Phe Asp Met Ser Cys Ile Lys Asp Val Ala Ile Lys Glu Pro Leu
        195                 200                 205

Val Asp Val Val Asp Pro Lys Gln Leu Val Thr Asn Ala Cys Leu Ile
    210                 215                 220

Lys Glu Val Asp Ile Tyr Thr Val Lys Val Glu Asp Leu Thr Phe Thr
225                 230                 235                 240

Ser Pro Phe Cys Leu Gln Val Lys Arg Asn Asp Tyr Val His Ala Leu
                245                 250                 255

Val Ala Tyr Phe Asn Ile Glu Phe Thr Arg Cys His Lys Arg Thr Gly
            260                 265                 270

Phe Ser Thr Ser Pro Glu Ser Pro Tyr Thr His Trp Lys Gln Thr Val
        275                 280                 285

Phe Tyr Met Glu Asp Tyr Leu Thr Val Lys Thr Gly Glu Glu Ile Phe
    290                 295                 300

Gly Thr Ile Gly Met Arg Pro Asn Ala Lys Asn Asn Arg Asp Leu Asp
305                 310                 315                 320

Phe Thr Ile Asp Leu Asp Phe Lys Gly Gln Leu Cys Glu Leu Ser Cys
                325                 330                 335

Ser Thr Asp Tyr Arg Met Arg
            340

<210> SEQ ID NO 3
<211> LENGTH: 20
<212> TYPE: DNA
<213> ORGANISM: Artificial
<220> FEATURE:
<223> OTHER INFORMATION: An artificially synthesized primer sequence for
      RT-PCR

<400> SEQUENCE: 3
gcaaattcca tggcaccgtc                                                   20

<210> SEQ ID NO 4
<211> LENGTH: 20
<212> TYPE: DNA
<213> ORGANISM: Artificial
<220> FEATURE:
<223> OTHER INFORMATION: An artificially synthesized primer sequence for
      RT-PCR

<400> SEQUENCE: 4
gcaaattcca tggcaccgtc                                                   20

<210> SEQ ID NO 5
<211> LENGTH: 20
<212> TYPE: DNA
<213> ORGANISM: Artificial
<220> FEATURE:
<223> OTHER INFORMATION: An artificially synthesized primer sequence for
      RT-PCR

<400> SEQUENCE: 5
```
tgggaacaag agggcatctg                                              20

<210> SEQ ID NO 6
<211> LENGTH: 22
<212> TYPE: DNA
<213> ORGANISM: Artificial
<220> FEATURE:
<223> OTHER INFORMATION: An artificially synthesized primer sequence for
      RT-PCR

<400> SEQUENCE: 6
ccaccactgc atcaaattca tg                                           22

<210> SEQ ID NO 7
<211> LENGTH: 24
<212> TYPE: DNA
<213> ORGANISM: Artificial
<220> FEATURE:
<223> OTHER INFORMATION: An artificially synthesized primer sequence for
      RT-PCR

<400> SEQUENCE: 7
gggctactgc ctcttctacg agtc                                         24

<210> SEQ ID NO 8
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 8
gtctttgtac tgccggtcct cgatg                                        25

<210> SEQ ID NO 9
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 9
ggtggacatc atcatcagcg agtgg                                        25

<210> SEQ ID NO 10
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 10
tcacatacag cgtggcccgg tctgg                                        25

<210> SEQ ID NO 11
<211> LENGTH: 19
<212> TYPE: DNA
<213> ORGANISM: Artificial
<220> FEATURE:
<223> OTHER INFORMATION: A target sequence for siRNA

<400> SEQUENCE: 11
gcagcacgac ttcttcaag                                               19

<210> SEQ ID NO 12
<211> LENGTH: 21
<212> TYPE: DNA
<213> ORGANISM: Artificial
<220> FEATURE:
<223> OTHER INFORMATION: An artificially synthesized oligonucleotide for
      siRNA

<400> SEQUENCE: 12
gcagcacgac uucuucaagt t                                            21

<210> SEQ ID NO 13
<211> LENGTH: 21
<212> TYPE: DNA
<213> ORGANISM: Artificial
<220> FEATURE:
<223> OTHER INFORMATION: An artificially synthesized oligonucleotide for
      siRNA

<400> SEQUENCE: 13
cuugaagaag ucgugcugct t                                            21

<210> SEQ ID NO 14
<211> LENGTH: 19
<212> TYPE: DNA
<213> ORGANISM: Artificial
<220> FEATURE:
<223> OTHER INFORMATION: A target sequence for siRNA

<400> SEQUENCE: 14
gtgcgctgct ggtgccaac                                               19

<210> SEQ ID NO 15
<211> LENGTH: 21
<212> TYPE: DNA
<213> ORGANISM: Artificial
<220> FEATURE:
<223> OTHER INFORMATION: An artificially synthesized oligonucleotide for
      siRNA

<400> SEQUENCE: 15
gugcgcugcu ggugccaact t                                            21

<210> SEQ ID NO 16
<211> LENGTH: 21
<212> TYPE: DNA
<213> ORGANISM: Artificial
<220> FEATURE:
<223> OTHER INFORMATION: An artificially synthesized oligonucleotide for
      siRNA

<400> SEQUENCE: 16
guuggcacca gcagcgcact t                                            21

<210> SEQ ID NO 17
<211> LENGTH: 19
<212> TYPE: DNA
<213> ORGANISM: Artificial
<220> FEATURE:
<223> OTHER INFORMATION: A target sequence for siRNA

<400> SEQUENCE: 17
gagttcacac gctgccaca                                               19

<210> SEQ ID NO 18
<211> LENGTH: 21
<212> TYPE: DNA

```
<213> ORGANISM: Artificial
<220> FEATURE:
<223> OTHER INFORMATION: An artificially synthesized oligonucleotide for
      siRNA

<400> SEQUENCE: 18
gaguucacac gcugccacat t                                              21

<210> SEQ ID NO 19
<211> LENGTH: 21
<212> TYPE: DNA
<213> ORGANISM: Artificial
<220> FEATURE:
<223> OTHER INFORMATION: An artificially synthesized oligonucleotide for
      siRNA

<400> SEQUENCE: 19
uguggcagcg ugugaacuct t                                              21
```